(12) United States Patent
Jackson et al.

(10) Patent No.: US 11,529,517 B2
(45) Date of Patent: Dec. 20, 2022

(54) ELECTRODE MOVEMENT DETECTION

(71) Applicant: Medtronic, Inc., Minneapolis, MN (US)

(72) Inventors: Jadin C. Jackson, Roseville, MN (US); Steven M. Goetz, North Oaks, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 17/036,641

(22) Filed: Sep. 29, 2020

(65) Prior Publication Data

US 2022/0096841 A1 Mar. 31, 2022

(51) Int. Cl.
*A61N 1/02* (2006.01)
*A61N 1/36* (2006.01)
*A61N 1/05* (2006.01)
*A61N 1/372* (2006.01)

(52) U.S. Cl.
CPC ......... *A61N 1/36139* (2013.01); *A61N 1/025* (2013.01); *A61N 1/0529* (2013.01); *A61N 1/36185* (2013.01); *A61N 1/36192* (2013.01); *A61N 1/37247* (2013.01)

(58) Field of Classification Search
CPC .. A61N 1/36139; A61N 1/025; A61N 1/0529; A61N 1/36185; A61N 1/36192; A61N 1/37247
See application file for complete search history.

(56) References Cited

U.S. PATENT DOCUMENTS

| 9,089,705 | B2 | 7/2015 | Zhu |
| 2003/0139781 | A1 | 7/2003 | Bradley et al. |
| 2007/0203537 | A1* | 8/2007 | Goetz ............... A61N 1/36185 607/59 |
| 2008/0125833 | A1* | 5/2008 | Bradley .............. A61N 1/3605 607/60 |
| 2014/0142549 | A1 | 5/2014 | Su et al. |
| 2016/0303376 | A1* | 10/2016 | Dinsmoor ........... A61B 5/4836 |
| 2017/0151437 | A1 | 6/2017 | Moffitt |
| 2018/0304075 | A1 | 10/2018 | Su et al. |
| 2019/0009098 | A1 | 1/2019 | Jiang et al. |
| 2019/0030321 | A1 | 1/2019 | Tinkhauser et al. |

(Continued)

FOREIGN PATENT DOCUMENTS

WO 2019204884 A1 10/2019

OTHER PUBLICATIONS

Tinkhauser et al., "Directional Local Field Potentials: A Tool to Optimize Deep Brain Stimulation", Movement Disorders, vol. 33, No. 1, Jan. 2018, pp. 159-164.

(Continued)

*Primary Examiner* — Ankit D Tejani
*Assistant Examiner* — Joshua Brendon Solomon
(74) *Attorney, Agent, or Firm* — Shumaker & Sieffert, P.A.

(57) ABSTRACT

Devices, systems, and techniques are disclosed for managing electrical stimulation therapy and/or sensing of physiological signals such as brain signals. For example, a system may assist a clinician in identifying one or more electrode combinations for sensing a brain signal. In another example, a user interface may display brain signal information and values of a stimulation parameter at least partially defining electrical stimulation delivered to a patient when the brain signal information was sensed.

24 Claims, 14 Drawing Sheets

(56) References Cited

U.S. PATENT DOCUMENTS

| | | |
|---|---|---|
| 2019/0134382 A1* | 5/2019 | Agnesi .............. A61N 1/37247 |
| 2019/0366074 A1 | 12/2019 | Carlton et al. |
| 2020/0038660 A1* | 2/2020 | Torgerson ............. A61B 5/686 |
| 2020/0078594 A1 | 3/2020 | Jiang et al. |

OTHER PUBLICATIONS

Matzel et al., "Sacral Neuromodulation: Standardized Electrode Placement Technique," Neuromodulation: Technology at the Neural Interface, Oct. 4, 2017, 9 pp.

International Search Report and Written Opinion of International Application No. PCT/US2021/052392, dated Jan. 28, 2022, 11 pp.

\* cited by examiner

ELECTRODE MOVEMENT DETECTION

TECHNICAL FIELD

This disclosure generally relates to electrical stimulation and recording.

BACKGROUND

Medical devices may be external or implanted, and may be used to deliver electrical stimulation therapy to various tissue sites of a patient to treat a variety of symptoms or conditions such as chronic pain, tremor, Parkinson's disease, other movement disorders, epilepsy, urinary or fecal incontinence, sexual dysfunction, obesity, or gastroparesis. A medical device may deliver electrical stimulation therapy via one or more leads that include electrodes located proximate to target locations associated with the brain, the spinal cord, pelvic nerves, peripheral nerves, or the gastrointestinal tract of a patient. Hence, electrical stimulation may be used in different therapeutic applications, such as deep brain stimulation (DBS), spinal cord stimulation (SCS), pelvic stimulation, gastric stimulation, or peripheral nerve field stimulation (PNFS).

A clinician may select values for a number of programmable parameters in order to define the electrical stimulation therapy to be delivered by the implantable stimulator to a patient. For example, the clinician may select one or more electrodes for delivery of the stimulation, a polarity of each selected electrode, a voltage or current amplitude, a pulse width, and a pulse frequency as stimulation parameters. A set of parameters, such as a set including electrode combination, electrode polarity, voltage or current amplitude, pulse width and pulse rate, may be referred to as a program in the sense that they define the electrical stimulation therapy to be delivered to the patient.

SUMMARY

In general, the disclosure describes devices, systems, and techniques for determining whether electrodes move with respect to tissue. For example, an implantable medical device (IMD) may be coupled to one or more leads carrying respective electrodes. The IMD may monitor electrical signals sensed by different electrode combinations over time (e.g., at multiple different times over minutes, hours, days, months or years). In response to determining that sensed electrical signals shift between the electrode combinations, the IMD may determine that the electrodes, and the lead carrying the electrodes, as shifted with respect to tissue. The sensed signals may be physiological signals generated by tissues at a particular location or generated directly by other electrodes at a location separate from the lead.

In an example, a lead may carry electrodes at different positions around a perimeter of the lead. If one electrode at one perimeter location senses an electric signal having a characteristic (e.g., an amplitude or spectral power) that previously was sensed by another electrode at a different perimeter location, the IMD may determine that the lead has rotated with respect to the tissue. The IMD may perform an action in response to detecting the lead movement, such as suspending therapy, adjusting electrode combinations used for delivering stimulation therapy, or transmitting an alert to an external device to inform a user that stimulation parameters may need to be adjusted to accommodate for the lead movement.

In one example, a method includes receiving, by processing circuitry, signal information indicative of first electrical signals sensed from a plurality of electrode combinations at a second time, each electrode combination comprising an electrode carried by a lead, wherein the lead defines a longitudinal axis and comprises a plurality of electrodes disposed at different positions around the longitudinal axis of the lead, determining, by the processing circuitry and based on the signal information and initial information indicative of second electrical signals sensed from the plurality of electrode combinations at a first time prior to the second time, that the lead has rotated with respect to tissue; and outputting, by the processing circuitry, an indication that the lead has rotated with respect to the tissue.

In another example, a system includes a memory configured to store initial information indicative of first electrical signals sensed from a plurality of electrode combinations at a first time, each electrode combination comprising an electrode carried by a lead, wherein the lead defines a longitudinal axis and comprises a plurality of electrodes disposed at different positions around the longitudinal axis of the lead, and processing circuitry configured to: receive signal information indicative of second electrical signals sensed from the plurality of electrode combinations at a second time after the first time; determine, based on the signal information, that the lead has rotated with respect to tissue; and outputting, an indication that the lead has rotated with respect to the tissue In another example, a computer-readable storage medium including instructions that, when executed, cause processing circuitry to receive signal information indicative of first electrical signals sensed from a plurality of electrode combinations at a second time, each electrode combination comprising an electrode carried by a lead, wherein the lead defines a longitudinal axis and comprises a plurality of electrodes disposed at different positions around the longitudinal axis of the lead; determine, based on the signal information and initial information indicative of second electrical signals sensed from the plurality of electrode combinations at a first time prior to the second time, that the lead has rotated with respect to tissue; and output an indication that the lead has rotated with respect to the tissue.

The details of one or more examples of the techniques of this disclosure are set forth in the accompanying drawings and the description below. Other features, objects, and advantages of the techniques will be apparent from the description and drawings, and from the claims.

DETAILED DESCRIPTION

Figure 1:
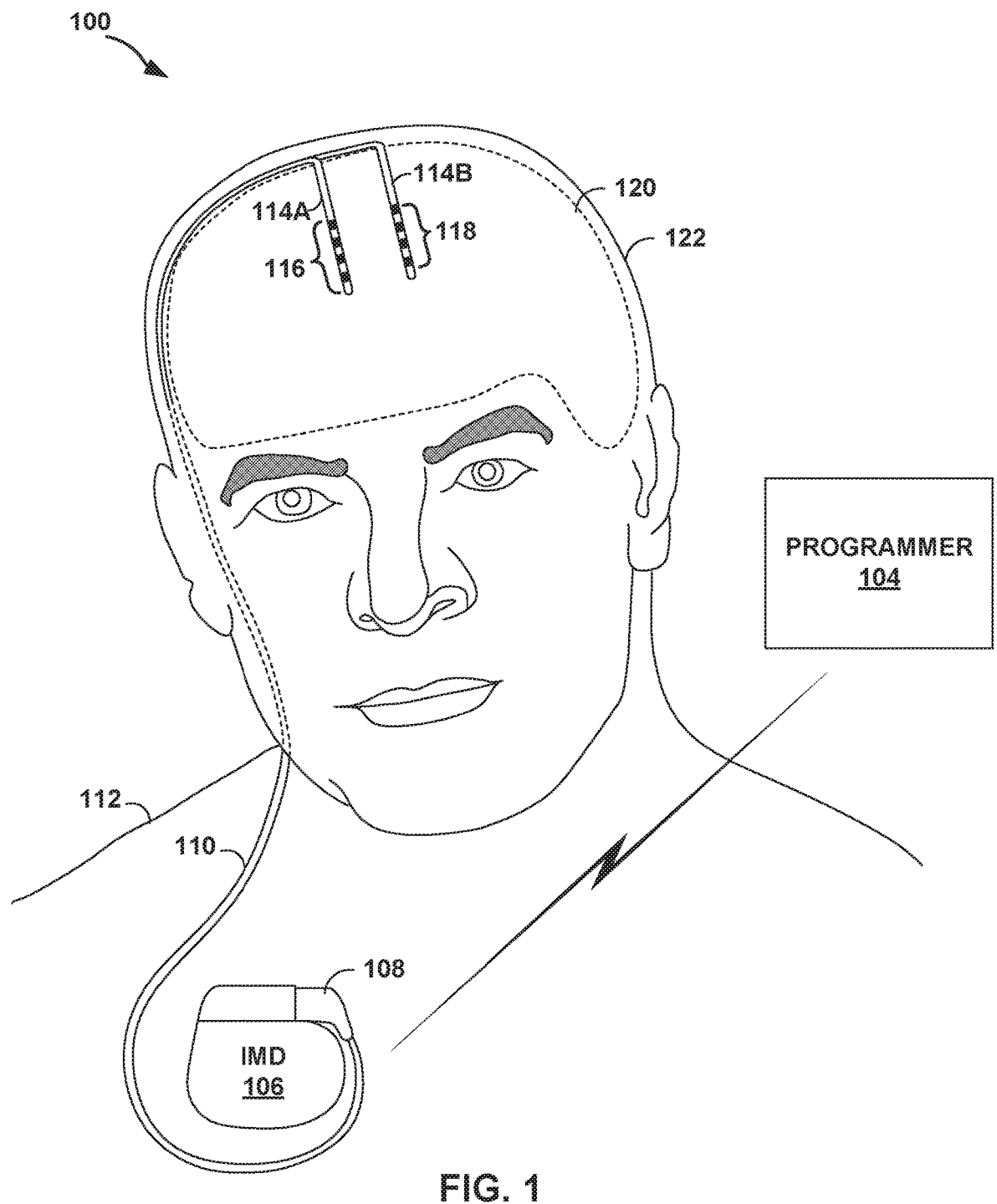
FIG. 1 is a conceptual diagram illustrating an example system that includes an implantable medical device (IMD) configured to deliver DBS to a patient according to an example of the techniques of the disclosure.

This disclosure describes various devices, systems, and techniques for determining that electrodes move with respect to tissue. A patient may suffer from one or more symptoms treatable by electrical stimulation therapy. For example, a patient may suffer from brain disorder such as Parkinson's disease, Alzheimer's disease, or another type of movement disorder. Deep brain stimulation (DBS) may be an effective treatment to reduce the symptoms associated with such disorders. However, efficacy of stimulation therapy may be reliant on selecting appropriate electrodes and other stimulation parameter values that direct an electric field to a target region of tissue. Stimulation of tissue outside of the target region may elicit undesirable effects and/or reduce the efficacy of the therapy. In addition, a lead, and the electrodes it carries, may move within tissue after implantation. Therefore, if a lead rotates about a longitudinal axis and/or shifts longitudinally within tissue after stimulation parameters are determined, the stimulation therapy may be less effective and/or the stimulation may result in undesirable side effects for the patient. I As described herein, various devices, systems, and techniques may determine whether electrodes, and the leads carrying the electrodes, move with respect to tissue. A lead may carry a plurality of electrodes at different longitudinal positions and, in some examples, at different positions around the longitudinal axis and the perimeter of the lead. An IMD may be configured to monitor electrical signals sensed by different electrode combinations over time. For example, the IMD may determine initial information representing electrical signals sensed by different electrode combinations at a first time, such as just after implantation or programming. The IMD may periodically (e.g., at regular intervals or in response to a trigger event indicative of a possible lead movement) determine other signal information representing electrical signals sensed by the different electrode combinations at a second time after the first time.

The initial information and the signal information may include one or more characteristics of the electrical signals for each electrode combination, such as an amplitude of the electrical signals, a spectral power of one or more frequency bands of the electrical signals, a ranking of each electrode combination with respect to an aspect of the electrical signals (e.g., amplitude), or some other characteristic of the electrical signals that differentiate the electrode combinations from each other. The electrical signals sensed by the electrode combinations may be intrinsic signals generated by tissue, signals generated by tissue evoked by a delivered stimulus, or a signal detected that was generated directly from a set of electrodes on a different lead. Since some electrode combinations on the lead will be closer to the spatial origin of the sensed electrical signals in tissue, characteristics such as signal amplitude will be larger for electrode combinations closer to the origin than for electrode combinations further from the origin.

If the lead does not move with respect to tissue, the initial information and the signal information for the electrode combinations between the first and second times should be substantially similar. For example, the electrode combination that has the highest amplitude at the first time would also sense the highest amplitude at the second time. However, if the lead, and the electrodes carried by the lead, move with respect to tissue (e.g., rotate or shift longitudinally), a different electrode combination will sense the highest amplitude signal. In this manner, the stronger electrical signals will "shift" from the electrode combinations previously closest to the origin of the electrical signals to different electrode combinations now closest to the origin after the lead moved with respect to tissue. In response to determining that the characteristics of electrical signals has shifted within the electrode combinations, the IMD may determine that the lead has rotated (and/or moved longitudinally) with respect to the tissue.

The IMD may perform an action in response to detecting the lead movement. For example, the IMD may suspend electrical stimulation therapy because the lead movement may result in different tissue being stimulated that could result in undesired effects for the patient. In some examples the IMD may automatically adjust electrode combinations used for delivering stimulation therapy (e.g., select new electrode combinations to compensate for the detected lead movement). In some examples, the IMD may transmit an alert to an external device (e.g., a programmer or networked server) to inform a user (e.g., the patient or a clinician) that stimulation parameters may need to be adjusted to compensate for the lead movement.

Although this disclosure is directed to DBS therapy, the systems, devices, and techniques described herein may similarly detect movement of leads and electrodes implanted outside of the brain, such as near other nerves or muscles for different diagnostic or therapeutic applications, such as spinal cord stimulation (SCS), pelvic stimulation, gastric stimulation, or peripheral nerve field stimulation (PNFS). Moreover, a human patient is described for example purposes herein, but similar systems, devices, and techniques may be used for other animals in other examples.

FIG. 1 is a conceptual diagram illustrating an example system 100 that includes an implantable medical device (IMD) 106 configured to deliver DBS to patient 122 according to an example of the techniques of the disclosure. As shown in the example of FIG. 1, example system 100 includes medical device programmer 104, implantable medical device (IMD) 106, lead extension 110, and leads 114A and 114B with respective sets of electrodes 116, 118. In the example shown in FIG. 1, electrodes 116, 118 of leads 114A, 114B are positioned to deliver electrical stimulation to a tissue site within brain 120, such as a deep brain site under the dura mater of brain 120 of patient 112. In some examples, delivery of stimulation to one or more regions of brain 120, such as the subthalamic nucleus, globus pallidus or thalamus, may be an effective treatment to manage movement disorders, such as Parkinson's disease. Some or all of electrodes 116, 118 also may be positioned to sense neurological brain signals within brain 120 of patient 112. In some examples, some of electrodes 116, 118 may be configured to sense neurological brain signals and others of electrodes 116, 118 may be configured to deliver adaptive electrical stimulation to brain 120. In other examples, all of electrodes 116, 118 are configured to both sense neurological brain signals and deliver adaptive electrical stimulation to brain 120.

IMD 106 includes a therapy module (e.g., which may include processing circuitry, signal generation circuitry or other electrical circuitry configured to perform the functions attributed to IMD 106) that includes a stimulation generator configured to generate and deliver electrical stimulation therapy to patient 112 via a subset of electrodes 116, 118 of leads 114A and 114B, respectively. The subset of electrodes 116, 118 that are used to deliver electrical stimulation to patient 112, and, in some cases, the polarity of the subset of electrodes 116, 118, may be referred to as a stimulation electrode combination. As described in further detail below, the stimulation electrode combination can be selected for a particular patient 112 and target tissue site (e.g., selected based on the patient condition). The group of electrodes 116, 118 includes at least one electrode and can include a plurality of electrodes. In some examples, the plurality of electrodes 116 and/or 118 may have a complex electrode geometry such that two or more electrodes of the lead are located at different positions around the perimeter of the respective lead (e.g., different positions around a longitudinal axis of the lead).

In some examples, the neurological signals (e.g., an example type of electrical signals) sensed within brain 120 may reflect changes in electrical current produced by the sum of electrical potential differences across brain tissue. Examples of neurological brain signals include, but are not limited to, electrical signals generated from local field potentials (LFP) sensed within one or more regions of brain 120, such as an electroencephalogram (EEG) signal, or an electrocorticogram (ECoG) signal. Local field potentials, however, may include a broader genus of electrical signals within brain 120 of patient 112.

In some examples, the neurological brain signals that are used to select a stimulation electrode combination may be sensed within the same region of brain 120 as the target tissue site for the electrical stimulation. As previously indicated, these tissue sites may include tissue sites within anatomical structures such as the thalamus, subthalamic nucleus or globus pallidus of brain 120, as well as other target tissue sites. The specific target tissue sites and/or regions within brain 120 may be selected based on the patient condition. Thus, due to these differences in target locations, in some examples, the electrodes used for delivering electrical stimulation may be different than the electrodes used for sensing neurological brain signals. In other examples, the same electrodes may be used to deliver electrical stimulation and sense brain signals. However, this configuration would require the system to switch between stimulation generation and sensing circuitry and may reduce the time the system can sense brain signals.

Electrical stimulation generated by IMD 106 may be configured to manage a variety of disorders and conditions. In some examples, the stimulation generator of IMD 106 is configured to generate and deliver electrical stimulation pulses to patient 112 via electrodes of a selected stimulation electrode combination. However, in other examples, the stimulation generator of IMD 106 may be configured to generate and deliver a continuous wave signal, e.g., a sine wave or triangle wave. In either case, a stimulation generator within IMD 106 may generate the electrical stimulation therapy for DBS according to a therapy program that is selected at that given time in therapy. In examples in which IMD 106 delivers electrical stimulation in the form of stimulation pulses, a therapy program may include a set of therapy parameter values (e.g., stimulation parameters), such as a stimulation electrode combination for delivering stimulation to patient 112, pulse frequency, pulse width, and a current or voltage amplitude of the pulses. As previously indicated, the electrode combination may indicate the specific electrodes 116, 118 that are selected to deliver stimulation signals to tissue of patient 112 and the respective polarities of the selected electrodes. IMD 106 may deliver electrical stimulation intended to contribute to a therapeutic effect. In some examples, IMD 106 may also, or alternatively, deliver electrical stimulation intended to be sensed by other electrode and/or elicit a physiological response, such as an evoked compound action potential (ECAP), that can be sensed by electrodes.

IMD 106 may be implanted within a subcutaneous pocket above the clavicle, or, alternatively, on or within cranium 122 or at any other suitable site within patient 112. Generally, IMD 106 is constructed of a biocompatible material that resists corrosion and degradation from bodily fluids. IMD 106 may comprise a hermetic housing to substantially enclose components, such as a processor, therapy module, and memory.

Figure 4A:
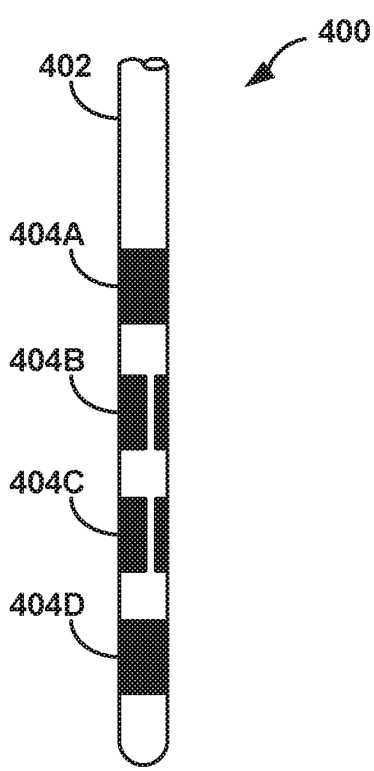
FIGS. 4A and 4B are conceptual diagrams of example leads with respective electrodes carried by the lead.
Figure 4B:
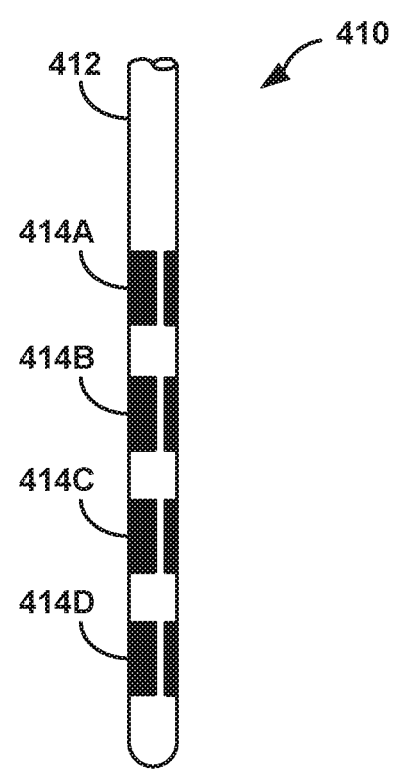

As shown in FIG. 1, implanted lead extension 110 is coupled to IMD 106 via connector 108 (also referred to as a connector block or a header of IMD 106). In the example of FIG. 1, lead extension 110 traverses from the implant site of IMD 106 and along the neck of patient 112 to cranium 122 of patient 112 to access brain 120. In the example shown in FIG. 1, leads 114A and 114B (collectively "leads 114") are implanted within the right and left hemispheres, respectively, of patient 112 in order deliver electrical stimulation to one or more regions of brain 120, which may be selected based on the patient condition or disorder controlled by therapy system 100. The specific target tissue site and the stimulation electrodes used to deliver stimulation to the target tissue site, however, may be selected, e.g., according to the identified patient behaviors and/or other sensed patient parameters. Other lead 114 and IMD 106 implant sites are contemplated. For example, IMD 106 may be implanted on or within cranium 122, in some examples. Or leads 114 may be implanted within the same hemisphere or IMD 106 may be coupled to a single lead implanted in a single hemisphere. Although leads 114 may have ring electrodes at different longitudinal positions as shown in FIG. 1, leads 114 may have electrodes disposed at different positions around the perimeter of the lead (e.g., different circumferential positions for a cylindrical shaped lead) as shown in the examples of FIGS. 4A and 4B.

Leads 114 illustrate an example lead set that include axial leads carrying ring electrodes disposed at different axial positions (or longitudinal positions). In other examples, leads may be referred to as "paddle" leads carrying planar arrays of electrodes on one side of the lead structure. In addition, as described herein, complex lead array geometries may be used in which electrodes are disposed at different respective longitudinal positions and different positions around the perimeter of the lead. As described herein, IMD 106 may be configured to detect movement of the lead with respect to tissue when monitoring electrical signals sensed by the different electrodes between different times.

Although leads 114 are shown in FIG. 1 as being coupled to a common lead extension 110, in other examples, leads 114 may be coupled to IMD 106 via separate lead extensions or directly to connector 108. Leads 114 may be positioned to deliver electrical stimulation to one or more target tissue sites within brain 120 to manage patient symptoms associated with a movement disorder of patient 112. Leads 114 may be implanted to position electrodes 116, 118 at desired locations of brain 120 through respective holes in cranium 122. Leads 114 may be placed at any location within brain 120 such that electrodes 116, 118 are capable of providing electrical stimulation to target tissue sites within brain 120 during treatment. For example, electrodes 116, 118 may be surgically implanted under the dura mater of brain 120 or within the cerebral cortex of brain 120 via a burr hole in cranium 122 of patient 112, and electrically coupled to IMD 106 via one or more leads 114.

In the example shown in FIG. 1, electrodes 116, 118 of leads 114 are shown as ring electrodes. Ring electrodes may be used in DBS applications because they are relatively simple to program and are capable of delivering an electrical field to any tissue adjacent to electrodes 116, 118. In other examples, electrodes 116, 118 may have different configurations. For example, in some examples, at least some of the electrodes 116, 118 of leads 114 may have a complex electrode array geometry that is capable of producing shaped electrical fields. The complex electrode array geometry may include multiple electrodes (e.g., partial ring or segmented electrodes) around the outer perimeter of each lead 114, rather than one ring electrode, such as shown in FIGS. 4A and 4B. In this manner, electrical stimulation may be directed in a specific direction from leads 114 to enhance therapy efficacy and reduce possible adverse side effects from stimulating a large volume of tissue. In some examples, a housing of IMD 106 may include one or more stimulation and/or sensing electrodes. In alternative examples, leads 114 may have shapes other than elongated cylinders as shown in FIG. 1. For example, leads 114 may be paddle leads, spherical leads, bendable leads, or any other type of shape effective in treating patient 112 and/or minimizing invasiveness of leads 114.

In the example shown in FIG. 1, IMD 106 includes a memory to store a plurality of therapy programs that each define a set of therapy parameter values. In some examples, IMD 106 may select a therapy program from the memory based on various parameters, such as sensed patient parameters and the identified patient behaviors. IMD 106 may generate electrical stimulation based on the selected therapy program to manage the patient symptoms associated with a movement disorder.

External programmer 104 wirelessly communicates with IMD 106 as needed to provide or retrieve therapy information. Programmer 104 is an external computing device that the user, e.g., a clinician and/or patient 112, may use to communicate with IMD 106. For example, programmer 104 may be a clinician programmer that the clinician uses to communicate with IMD 106 and program one or more therapy programs for IMD 106. Alternatively, programmer 104 may be a patient programmer that allows patient 112 to select programs and/or view and modify therapy parameters. The clinician programmer may include more programming features than the patient programmer. In other words, more complex or sensitive tasks may only be allowed by the clinician programmer to prevent an untrained patient from making undesirable changes to IMD 106. IMD 106 may also transmit notifications to programmer 104 for delivery to a user in response to detecting that one of leads 114 has moved with respect to tissue. Programmer 104 may enter a new programming session for the user to select new stimulation parameters for subsequent therapy.

When programmer 104 is configured for use by the clinician, programmer 104 may be used to transmit initial programming information to IMD 106. This initial information may include hardware information, such as the type of leads 114 and the electrode arrangement, the position of leads 114 within brain 120, the configuration of electrode array 116, 118, initial programs defining therapy parameter values, and any other information the clinician desires to program into IMD 106. Programmer 104 may also be capable of completing functional tests (e.g., measuring the impedance of electrodes 116, 118 of leads 114). In some examples, programmer 104 may receive sensed signals or representative information and perform the same techniques and functions attributed to IMD 106 herein. In other examples, a remote server (e.g., a standalone server or part of a cloud service) may perform the functions attributed to IMD 106, programmer 104, or any other devices described herein.

The clinician may also store therapy programs within IMD 106 with the aid of programmer 104. During a programming session, the clinician may determine one or more therapy programs that may provide efficacious therapy to patient 112 to address symptoms associated with the patient condition, and, in some cases, specific to one or more different patient states, such as a sleep state, movement state or rest state. For example, the clinician may select one or more stimulation electrode combination with which stimulation is delivered to brain 120. During the programming session, the clinician may evaluate the efficacy of the specific program being evaluated based on feedback provided by patient 112 or based on one or more physiological parameters of patient 112 (e.g., muscle activity, muscle tone, rigidity, tremor, etc.). Alternatively, identified patient behavior from video information may be used as feedback during the initial and subsequent programming sessions. Programmer 104 may assist the clinician in the creation/identification of therapy programs by providing a methodical system for identifying potentially beneficial therapy parameter values.

Programmer 104 may also be configured for use by patient 112. When configured as a patient programmer, programmer 104 may have limited functionality (compared to a clinician programmer) in order to prevent patient 112 from altering critical functions of IMD 106 or applications that may be detrimental to patient 112. In this manner, programmer 104 may only allow patient 112 to adjust values for certain therapy parameters or set an available range of values for a particular therapy parameter.

Programmer 104 may also provide an indication to patient 112 when therapy is being delivered, when patient input has triggered a change in therapy or when the power source within programmer 104 or IMD 106 needs to be replaced or recharged. For example, programmer 112 may include an alert LED, may flash a message to patient 112 via a programmer display, generate an audible sound or somatosensory cue to confirm patient input was received, e.g., to indicate a patient state or to manually modify a therapy parameter.

Therapy system 100 may be implemented to provide chronic stimulation therapy to patient 112 over the course of several months or years. However, system 100 may also be employed on a trial basis to evaluate therapy before committing to full implantation. If implemented temporarily, some components of system 100 may not be implanted within patient 112. For example, patient 112 may be fitted with an external medical device, such as a trial stimulator, rather than IMD 106. The external medical device may be coupled to percutaneous leads or to implanted leads via a percutaneous extension. If the trial stimulator indicates DBS system 100 provides effective treatment to patient 112, the clinician may implant a chronic stimulator within patient 112 for relatively long-term treatment.

Although IMD 106 is described as delivering electrical stimulation therapy to brain 120, IMD 106 may be configured to direct electrical stimulation to other anatomical regions of patient 112 in other examples. In other examples, system 100 may include an implantable drug pump in addition to, or in place of, IMD 106. Further, an IMD may provide other electrical stimulation such as spinal cord stimulation to treat a movement disorder.

According to the techniques of the disclosure, system 100 may determine whether a lead has shifted, or moved, with respect to the tissue within which the lead is implanted. For example, IMD 106 may include a memory configured to store initial information indicative of first electrical signals sensed from a plurality of electrode combinations at a first time. Sensing circuitry within IMD 106 may sense the potential difference between respective electrode combinations. The electrode combinations may include only two or more electrodes on the same lead (e.g., bipolar sensing). In this manner, the first electrical signals and the second electrical signals may include differential signals between respective electrode combinations of the plurality of electrode combinations. In other examples, an electrode combination may include at least one electrode from two different leads. In another example, the electrical signals may be sensed via monopolar sensing where each electrode combination includes one electrode from a lead and an indifferent electrode (e.g., an electrode or conductive surface on IMD 106 housing or set at some distance away from the lead) that is relatively far from the electrode. In this manner, the first electrical signals and the second electrical signals may include monopolar signals between respective electrode combinations of the plurality of electrode combinations. In any type of sensing, the same type of sensing may be used for generating the initial information and later generating signal information based on electrical signals sensed at a second time after the first time. In one example, each electrode combination includes an electrode carried by a lead, where the lead defines a longitudinal axis and includes a plurality of electrodes disposed at different positions around the longitudinal axis of the lead (e.g., leads 400 and 410 of FIGS. 4A and 4B).

System 100 (e.g., IMD 106) may also include processing circuitry configured to receive signal information indicative of second electrical signals sensed from the plurality of electrode combinations at a second time after the first time. The processing circuitry or sensing circuitry may generate the signal information based on the sensing circuitry sensing potential differences for each electrode combination. IMD 106 may then determine, based on the signal information, that the lead has rotated with respect to tissue and then output an indication that the lead has rotated with respect to the tissue.

In general, IMD 106 (or another device, such as programmer 104) may determine that the lead has moved with respect to tissue when the subsequent signal information indicates that different electrode combinations associated with the lead are detecting electrical signals that previously were detected by other electrode combinations. In this manner, IMD 106 may determine that the expected characteristics of the sensed electrical signals have "shifted" from one set of electrode combinations to a different set of electrode combinations. In one example, the characteristic of the electrical signals used to identify this shift may be an amplitude of the electrical signals. IMD 106 may determine that the lead has rotated by comparing first amplitudes of the initial information for the plurality of electrode combinations to second amplitudes of the signal information for the plurality of electrode combinations. IMD 106 may determine, based on the comparison, that the first amplitudes of the initial information do not match the second amplitudes of the signal information for respective electrode configurations. For example, one electrode that had that highest amplitude in the initial information no longer has the highest amplitude. Instead, a different electrode at a different circumferential position now sensed the highest amplitude of the electrode combinations. IMD 106 may then determine, based on determination that the first amplitudes do not match the second amplitudes, that the lead has rotated.

Instead of signal amplitude, IMD 106 may analyze different characteristics of the sensed electrical signals. The amplitude may be an absolute amplitude, a normalized amplitude, a categorized amplitude (e.g., amplitude values fall within separate predetermined ranges), or a ranked amplitude. In another example, IMD 106 may determine spatial derivatives between different electrodes. For example, the spatial derivative may be a first spatial derivative or a second spatial derivative computed using the differences in differential recordings between electrodes. The second spatial derivative may be representative of the current source density which may indicate the proximity of the electrode with respect to the signal source (e.g., the target anatomy). In other examples, the characteristic may be a spectral power. The spectral power may be a power for one or more frequency bands of the electrical signal. For example, IMD 106 may calculate the power of the beta frequency band for each sensed electrical signal, which may indicate the proximity of each electrode combination to a target neural location expected to generate signals in the beta frequency band. In some examples, IMD 106 may determine a rank for each electrode or electrode combination for any of the above-referenced parameters to determine if the rank of the electrodes changes between measurements. In other examples, IMD 106 or other device may determine the three dimensional position of the signal source with respect to the lead based on signal measurements of electrodes at two or more time points that may indicate direct estimates of rotational change or translational shift.

In some examples, IMD 106 may generate a matrix representing the characteristics of the sensed electrical signals (e.g., signal amplitudes) for each of the electrode combinations. In this manner, the initial information may include a first matrix representing signal amplitudes sensed by respective electrode combinations of the plurality of electrode combinations at the first time, and the signal information comprises a second matrix representing signal amplitudes sensed by respective electrode combinations of the plurality of electrode combinations at the second time. IMD 106 may compare the first and second matrices to determine if any shift has occurred in between the matrices and, by extension, determine if a shift in lead location occurred. In some examples, IMD 106 may include a table of pre-computed rotations and shifts of the electrodes in memory to limit the computational power required to compare matrices. IMD 106 may perform the comparison using a cost-function to maximize the correlation of the sensed signals to the table. For example, the cost may equal 1−corr(current matrix, previous matrix). In this manner, IMD 106 may compare the sensed signals to the table of pre-computed rotations to identify the most probable lead rotations and/or shifts.

IMD 106 may determine that the lead shifted in any direction according to the changes in electrical signals sensed by each electrode combination. When the electrodes are disposed at different positions around the longitudinal axis of the lead, IMD 106 may determine that the lead has rotated about the longitudinal axis. In addition, or alternatively, IMD 106 may determine that the lead has shifted longitudinally with respect to tissue. For example, a different electrode combination disposed closer to a distal end of the lead than a previous electrode combination may have sensed electrical signals with the highest amplitude at the second time for measurement. IMD 106 may sense signals to determine lead rotation or shift when the patient is in a known or stable state. For example, IMD 106 may determine that the patient is at rest (e.g., according to one or more accelerometers, heart rate detectors, oxygen saturation, etc.) and only sense signals during this time. In some examples, IMD 106 may transmit a request to the external programmer to request that the patient remains at rest and obtain sensed signals in response to receiving confirmation from the external programmer that the patient is at rest. IMD 106 may pause delivery of stimulation therapy when sensing signals for determining lead movement. In some examples, IMD 106 may sense signals for determining lead movement during a period in which the patient has turned off stimulation delivery or that adaptive therapy is in a non-delivery mode.

In response to IMD 106 determining that the lead has moved, IMD 106 may perform an action. For example, IMD 106 may control a display to present the indication to a user that the lead has rotated with respect to the tissue. Controlling the display may involve transmitting an alert to external programmer 104 which in turn presents the alert on the display of programmer 104. In some examples, IMD 106 may transmit a request to a user to update stimulation parameter values that define electrical stimulation because the moved lead may no longer provide sufficiency therapy to the patient and/or cause undesirable side effects. In this manner, programmer 104 may receive updated stimulation parameter values (e.g., a different electrode combination to use for stimulation and/or recording) and transmit the updated stimulation parameters back to IMD 106. IMD 106 may then the receive updated stimulation parameters that define electrical stimulation and control stimulation circuitry of IMD 106 to deliver the electrical stimulation according to the updated stimulation parameters. In some examples, IMD 106 or programmer 104 may check whether pre-programmed groups or other parameter sets remain safe or effective with the changed electrode locations in response to determining that the lead has moved. In some examples, IMD 106 and/or programmer 104 can confirm available parameter ranges are safe or appropriate with the moved lead or alert a user when the moved lead is no longer compatible with the new lead position. IMD 106 and/or programmer 104 may inform the user directly or via a cloud-connected platform, for example. Alternatively, IMD 106 and/or programmer 104 may adjust available parameter value ranges in response to the changed electrode locations (e.g., due to the rotation and/or shift).

The architecture of system 100 illustrated in FIG. 1 is shown as an example. The techniques as set forth in this disclosure may be implemented in the example system 100 of FIG. 1, as well as other types of systems not described specifically herein. Nothing in this disclosure should be construed so as to limit the techniques of this disclosure to the example architecture illustrated by FIG. 1.

Figure 2:
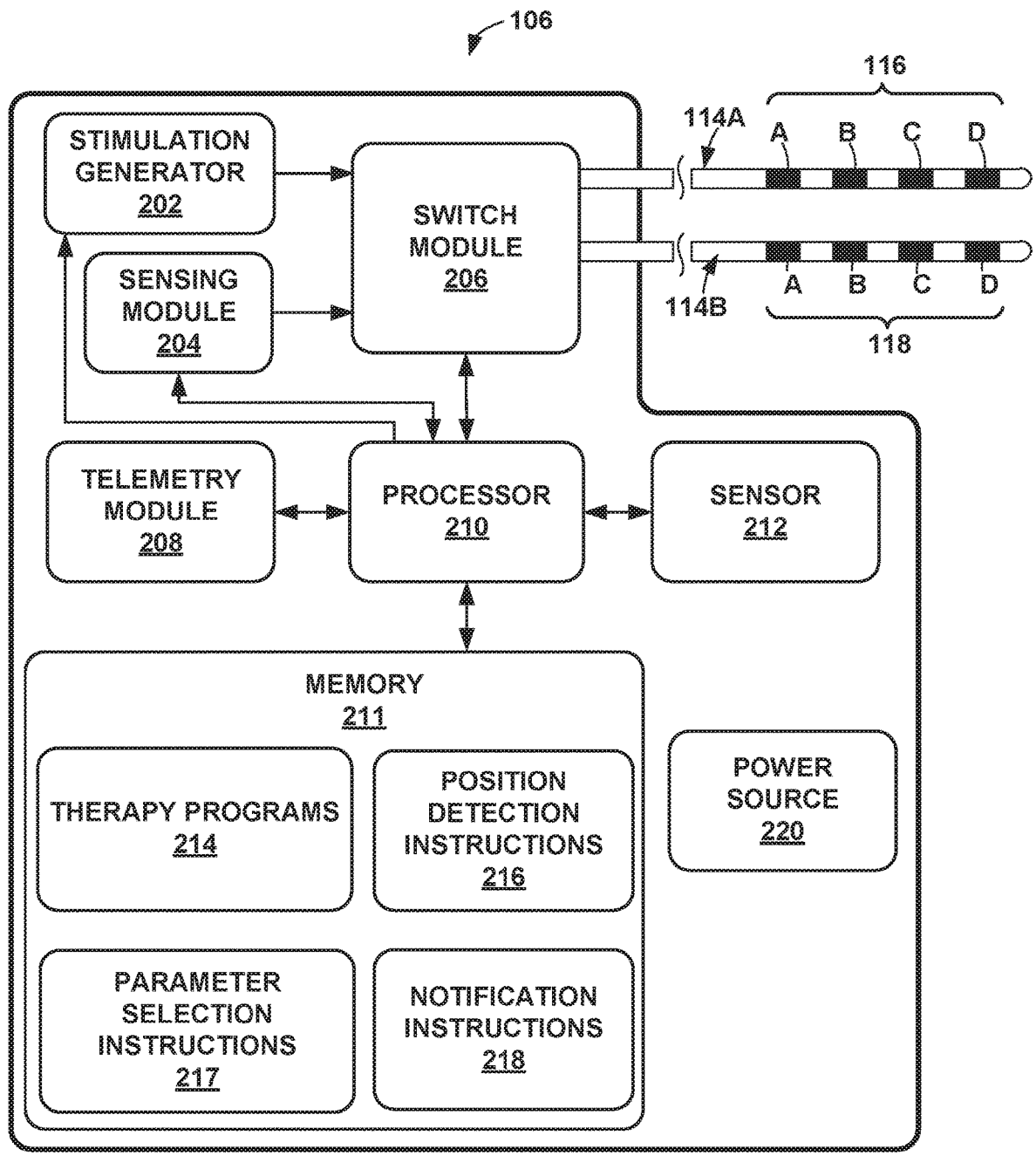
FIG. 2 is a block diagram of the example IMD of FIG. 1 for delivering DBS therapy according to an example of the techniques of the disclosure.

FIG. 2 is a block diagram of the example IMD 106 of FIG. 1 for delivering DBS therapy. In the example shown in FIG. 2, IMD 106 includes processor 210, memory 211, stimulation generator 202, sensing module 204, switch module 206, telemetry module 208, sensor 212, and power source 220. Each of these modules may be or include electrical circuitry configured to perform the functions attributed to each respective module. For example, processor 210 may include processing circuitry, switch module 206 may include switch circuitry, sensing module 204 may include sensing circuitry, and telemetry module 208 may include telemetry circuitry. Switch module 204 may not be necessary for multiple current source and sink configurations. Memory 211 may include any volatile or non-volatile media, such as a random-access memory (RAM), read only memory (ROM), non-volatile RAM (NVRAM), electrically erasable programmable ROM (EEPROM), flash memory, and the like. Memory 211 may store computer-readable instructions that, when executed by processor 210, cause IMD 106 to perform various functions. Memory 211 may be a storage device or other non-transitory medium.

In the example shown in FIG. 2, memory 211 stores therapy programs 214 that include respective stimulation parameter sets that define therapy. Each stored therapy program 214 defines a particular set of electrical stimulation parameters (e.g., a therapy parameter set), such as a stimulation electrode combination, electrode polarity, current or voltage amplitude, pulse width, and pulse rate. In some examples, individual therapy programs may be stored as a therapy group, which defines a set of therapy programs with which stimulation may be generated. The stimulation signals defined by the therapy programs of the therapy group may be delivered together on an overlapping or non-overlapping (e.g., time-interleaved) basis.

Memory 211 may also include position detection instructions 216 that define the process by which processor 210 determines whether the lead has moved with respect to tissue. Position detection instructions 216 may also include instructions that define the frequency with which processor 210 controls sensing electrical signals and determining one or more characteristics of the electrical signals that are used to monitor if electrode combinations sensing changes. Memory 211 may also include parameter selection instructions 217 and notification instructions 218. Parameter selection instructions 217 may include instructions that control processor 210 selecting different stimulation parameter values such as electrode combinations, amplitudes, pulse frequencies, or other parameter values for compensating for lead movement. Notification instructions 218 may define instructions that control processor 210 actions such as transmitting an alert or other notification to an external device, such as programmer 104, that indicates the lead has moved with respect to tissue. In some examples, notification instructions 218 may also define additional information that processor 210 transmits with the alert, such as an indication of which direction the lead moved, proposed electrode combinations closest to the target tissue after lead movement, or any other information that may assist the user in selecting new stimulation parameters.

In some examples, the sense and stimulation electrode combinations may include the same subset of electrodes 116, 118, a housing of IMD 106 functioning as an electrode, or may include different subsets or combinations of such electrodes. Thus, memory 211 can store a plurality of sense electrode combinations and, for each sense electrode combination, store information identifying the stimulation electrode combination that is associated with the respective sense electrode combination. The associations between sense and stimulation electrode combinations can be determined, e.g., by a clinician or automatically by processor 210. In some examples, corresponding sense and stimulation electrode combinations may comprise some or all of the same electrodes. In other examples, however, some or all of the electrodes in corresponding sense and stimulation electrode combinations may be different. For example, a stimulation electrode combination may include more electrodes than the corresponding sense electrode combination in order to increase the efficacy of the stimulation therapy. In some examples, as discussed above, stimulation may be delivered via a stimulation electrode combination to a tissue site that is different than the tissue site closest to the corresponding sense electrode combination but is within the same region, e.g., the thalamus, of brain 120 in order to mitigate any irregular oscillations or other irregular brain activity within the tissue site associated with the sense electrode combination. In other examples, the electrodes that deliver stimulation may be carried by a lead implanted in a different region of the brain than a different lead that carries the sensing electrodes.

Stimulation generator 202, under the control of processor 210, generates stimulation signals for delivery to patient 112 via selected combinations of electrodes 116, 118. An example range of electrical stimulation parameters believed to be effective in DB S to manage a movement disorder of patient include:

1. Pulse Rate, i.e., Frequency: between approximately 0.1 Hertz and approximately 500 Hertz, such as between approximately 0.1 to 10 Hertz, approximately 40 to 185 Hertz, or such as approximately 140 Hertz.

2. In the case of a voltage controlled system, Voltage Amplitude: between approximately 0.1 volts and approximately 50 volts, such as between approximately 2 volts and approximately 3 volts.

3. In the alternative case of a current controlled system, Current Amplitude: between approximately 0.2 milliamps to approximately 100 milliamps, such as between approximately 1.3 milliamps and approximately 2.0 milliamps.

4. Pulse Width: between approximately 10 microseconds and approximately 5000 microseconds, such as between approximately 100 microseconds and approximately 1000 microseconds, or between approximately 180 microseconds and approximately 450 microseconds.

Accordingly, in some examples, stimulation generator 202 generates electrical stimulation signals in accordance with the electrical stimulation parameters noted above. Other ranges of therapy parameter values may also be useful, and may depend on the target stimulation site within patient 112. While stimulation pulses are described, stimulation signals may be of any form, such as continuous-time signals (e.g., sine waves) or the like. Stimulation signals configured to elicit ECAPs or other evoked physiological signals may be similar or different from the above parameter value ranges.

Processor 210 may include fixed function processing circuitry and/or programmable processing circuitry, and may comprise, for example, any one or more of a microprocessor, a controller, a digital signal processor (DSP), an application specific integrated circuit (ASIC), a field-programmable gate array (FPGA), discrete logic circuitry, or any other processing circuitry configured to provide the functions attributed to processor 210 herein may be embodied as firmware, hardware, software or any combination thereof.

Processor 210 may control stimulation generator 202 according to therapy programs 214 stored in memory 211 to apply particular stimulation parameter values specified by one or more of programs, such as voltage amplitude or current amplitude, pulse width, or pulse rate.

In the example shown in FIG. 2, the set of electrodes 116 includes electrodes 116A, 116B, 116C, and 116D, and the set of electrodes 118 includes electrodes 118A, 118B, 118C, and 118D. Processor 210 also controls switch module 206 to apply the stimulation signals generated by stimulation generator 202 to selected combinations of electrodes 116, 118. In particular, switch module 204 may couple stimulation signals to selected conductors within leads 114, which, in turn, deliver the stimulation signals across selected electrodes 116, 118. Switch module 206 may be a switch array, switch matrix, multiplexer, or any other type of switching module configured to selectively couple stimulation energy to selected electrodes 116, 118 and to selectively sense neurological brain signals with selected electrodes 116, 118. Hence, stimulation generator 202 is coupled to electrodes 116, 118 via switch module 206 and conductors within leads 114. In some examples, however, IMD 106 does not include switch module 206.

Stimulation generator 202 may be a single channel or multi-channel stimulation generator. In particular, stimulation generator 202 may be capable of delivering a single stimulation pulse, multiple stimulation pulses, or a continuous signal at a given time via a single electrode combination or multiple stimulation pulses at a given time via multiple electrode combinations. In some examples, however, stimulation generator 202 and switch module 206 may be configured to deliver multiple channels on a time-interleaved basis. For example, switch module 206 may serve to time divide the output of stimulation generator 202 across different electrode combinations at different times to deliver multiple programs or channels of stimulation energy to patient 112. Alternatively, stimulation generator 202 may comprise multiple voltage or current sources and sinks that are coupled to respective electrodes to drive the electrodes as cathodes or anodes. In this example, IMD 106 may not require the functionality of switch module 206 for time-interleaved multiplexing of stimulation via different electrodes.

Electrodes 116, 118 on respective leads 114 may be constructed of a variety of different designs. For example, one or both of leads 114 may include two or more electrodes at each longitudinal location along the length of the lead, such as multiple electrodes at different perimeter locations around the perimeter of the lead at each of the locations A, B, C, and D. On one example, the electrodes may be electrically coupled to switch module 206 via respective wires that are straight or coiled within the housing the lead and run to a connector at the proximal end of the lead. In another example, each of the electrodes of the lead may be electrodes deposited on a thin film. The thin film may include an electrically conductive trace for each electrode that runs the length of the thin film to a proximal end connector. The thin film may then be wrapped (e.g., a helical wrap) around an internal member to form the lead 114. These and other constructions may be used to create a lead with a complex electrode geometry.

Although sensing module 204 is incorporated into a common housing with stimulation generator 202 and processor 210 in FIG. 2, in other examples, sensing module 204 may be in a separate housing from IMD 106 and may communicate with processor 210 via wired or wireless communication techniques. Example neurological brain signals include, but are not limited to, a signal generated from local field potentials (LFPs) within one or more regions of brain 28. EEG and ECoG signals are examples of local field potentials that may be measured within brain 120. However, local field potentials may include a broader genus of electrical signals within brain 120 of patient 112. Instead of, or in addition to, LFPs, IMD 106 may be configured to detect patterns of single-unit activity and/or multi-unit activity. IMD 106 may sample this activity at rates above 1,000 Hz, and in some examples within a frequency range of 6,000 Hz to 40,000 Hz. IMD 106 may identify the wave-shape of single units and/or an envelope of unit modulation that may be features used to differentiate or rank electrodes. In some examples, this technique may include phase-amplitude coupling to the envelope or to specific frequency bands in the LFPs sensed from the same or different electrodes.

Sensor 212 may include one or more sensing elements that sense values of a respective patient parameter. For example, sensor 212 may include one or more accelerometers, optical sensors, chemical sensors, temperature sensors, pressure sensors, or any other types of sensors. Sensor 212 may output patient parameter values that may be used as feedback to control delivery of therapy. IMD 106 may include additional sensors within the housing of IMD 106 and/or coupled via one of leads 114 or other leads. In addition, IMD 106 may receive sensor signals wirelessly from remote sensors via telemetry module 208, for example. In some examples, one or more of these remote sensors may be external to patient (e.g., carried on the external surface of the skin, attached to clothing, or otherwise positioned external to the patient). For example, IMD 106 may determine from these one or more additional sensors the brain state of the patient and sense signals for determining electrode movement during a brain state of lower fluctuation or lower noise to improve signal detection. In other examples, IMD 106 may employ an inertial sensor to determine when the patient is at rest (e.g., lying down and/or sleeping) and sense signals for determining lead movement during a time of rest to reduce noise or other motion artifacts in the sensed signals. In some examples, IMD 106 may sense signals for determining lead movement in response to receiving an indication that the patient received a dose of medication or the patient has entered a physician appointment.

Telemetry module 208 supports wireless communication between IMD 106 and an external programmer 104 or another computing device under the control of processor 210. Processor 210 of IMD 106 may receive, as updates to programs, values for various stimulation parameters such as magnitude and electrode combination, from programmer 104 via telemetry module 208. The updates to the therapy programs may be stored within therapy programs 214 portion of memory 211. In addition, processor 210 may control telemetry module 208 to transmit alerts or other information to programmer 104 that indicate a lead moved with respect to tissue. Telemetry module 208 in IMD 106, as well as telemetry modules in other devices and systems described herein, such as programmer 104, may accomplish communication by radiofrequency (RF) communication techniques. In addition, telemetry module 208 may communicate with external medical device programmer 104 via proximal inductive interaction of IMD 106 with programmer 104. Accordingly, telemetry module 208 may send information to external programmer 104 on a continuous basis, at periodic intervals, or upon request from IMD 106 or programmer 104.

Power source 220 delivers operating power to various components of IMD 106. Power source 220 may include a small rechargeable or non-rechargeable battery and a power generation circuit to produce the operating power. Recharging may be accomplished through proximal inductive interaction between an external charger and an inductive charging coil within IMD 220. In some examples, power requirements may be small enough to allow IMD 220 to utilize patient motion and implement a kinetic energy-scavenging device to trickle charge a rechargeable battery. In other examples, traditional batteries may be used for a limited period of time.

According to the techniques of the disclosure, processor 210 of IMD 106 delivers, electrodes 116, 118 interposed along leads 114 (and optionally switch module 206), electrical stimulation therapy to patient 112. The DBS therapy is defined by one or more therapy programs 214 having one or more parameters stored within memory 211. For example, the one or more parameters include a current amplitude (for a current-controlled system) or a voltage amplitude (for a voltage-controlled system), a pulse rate or frequency, and a pulse width, or quantity of pulses per cycle. In examples where the electrical stimulation is delivered according to a "burst" of pulses, or a series of electrical pulses defined by an "on-time" and an "off-time," the one or more parameters may further define one or more of a number of pulses per burst, an on-time, and an off-time.

In some examples, sensing module 204 may sense an electrical signal that is a neurological signal (e.g., a LFP signal) within the Beta frequency band of brain 120 of patient 112. The signal within the Beta frequency band of patient 112 may correlate to one or more symptoms of Parkinson's disease in patient 112. Generally speaking, neurological signals within the Beta frequency band of patient 112 may be approximately proportional to the severity of the symptoms of patient 112. For example, as tremor induced by Parkinson's disease increases, one or more of electrodes 116, 118 detect an increase in the magnitude of neurological signals within the Beta frequency band of patient 112. In this manner, the closest electrode combination to the origin of this neurological signal may be selected for therapy. When a lead rotates or shifts longitudinally, a different electrode combination may be best positioned to stimulate the tissue generating the neurological signal indicative of patient symptoms or of patient side-effects. Therefore, as described herein, processor 210 determines when this shift occurs with the electrodes and determines that the lead has moved. Processor 210 may automatically adjust the electrode combination for delivering therapy and/or other stimulation parameter values to compensate for the moved lead. Alternatively, processor 210 may transmit an alert to programmer 104 or other external device to indicate that updated stimulation parameters may be needed to continue efficacious therapy. For example, if the adjustments to electrode combinations and/or stimulation parameter values to compensate for the moved lead fall within respective ranges approved by the clinician, processor 210 may automatically adjust the electrode combination and/or other stimulation parameter values. If the adjustments to electrode combinations and/or stimulation parameter values to compensate for the moved lead do not fall within respective ranges approved by the clinician, processor 210 may communicate with programmer 104 to request approval or parameter values from a user.

Figure 3:
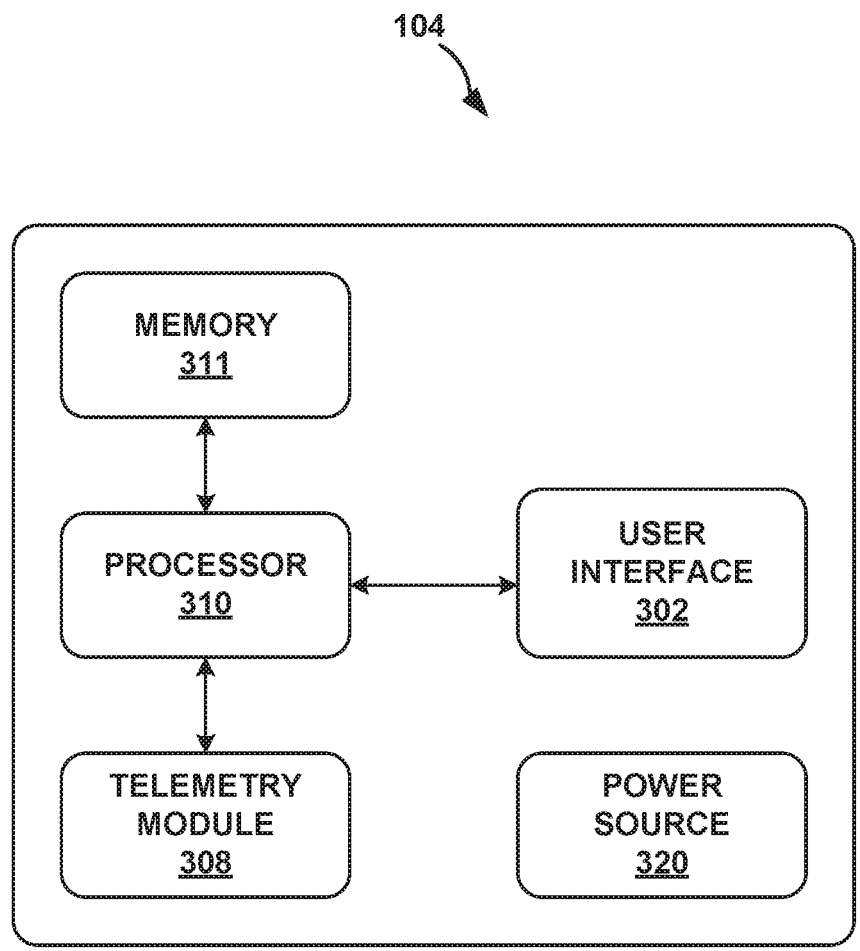
FIG. 3 is a block diagram of the external programmer of FIG. 1 for controlling delivery of DBS therapy according to an example of the techniques of the disclosure.

FIG. 3 is a block diagram of the external programmer 104 of FIG. 1 for controlling delivery of DBS therapy according to an example of the techniques of the disclosure. Although programmer 104 may generally be described as a hand-held device, programmer 104 may be a larger portable device or a more stationary device. In some examples, programmer 104 may be referred to as a tablet computing device. In addition, in other examples, programmer 104 may be included as part of a bed-side monitor, an external charging device or include the functionality of an external charging device. As illustrated in FIG. 3, programmer 104 may include a processor 310, memory 311, user interface 302, telemetry module 308, and power source 320. Memory 311 may store instructions that, when executed by processor 310, cause processor 310 and external programmer 104 to provide the functionality ascribed to external programmer 104 throughout this disclosure. Each of these components, or modules, may include electrical circuitry that is configured to perform some or all of the functionality described herein. For example, processor 310 may include processing circuitry configured to perform the processes discussed with respect to processor 310.

In general, programmer 104 comprises any suitable arrangement of hardware, alone or in combination with software and/or firmware, to perform the techniques attributed to programmer 104, and processor 310, user interface 302, and telemetry module 308 of programmer 104. In various examples, programmer 104 may include one or more processors, which may include fixed function processing circuitry and/or programmable processing circuitry, as formed by, for example, one or more microprocessors, DSPs, ASICs, FPGAs, or any other equivalent integrated or discrete logic circuitry, as well as any combinations of such components. Programmer 104 also, in various examples, may include a memory 311, such as RAM, ROM, PROM, EPROM, EEPROM, flash memory, a hard disk, a CD-ROM, comprising executable instructions for causing the one or more processors to perform the actions attributed to them. Moreover, although processor 310 and telemetry module 308 are described as separate modules, in some examples, processor 310 and telemetry module 308 may be functionally integrated with one another. In some examples, processor 310 and telemetry module 308 correspond to individual hardware units, such as ASICs, DSPs, FPGAs, or other hardware units.

Memory 311 (e.g., a storage device) may store instructions that, when executed by processor 310, cause processor 310 and programmer 104 to provide the functionality ascribed to programmer 104 throughout this disclosure. For example, memory 311 may include instructions that cause processor 310 to obtain a parameter set from memory, select a spatial electrode movement pattern, provide an interface that recommends or otherwise facilitates parameter value selection, or receive a user input and send a corresponding command to IMD 106, or instructions for any other functionality. In addition, memory 311 may include a plurality of programs, where each program includes a parameter set that defines stimulation therapy.

User interface 302 may include a button or keypad, lights, a speaker for voice commands, a display, such as a liquid crystal (LCD), light-emitting diode (LED), or organic light-emitting diode (OLED). In some examples the display may be a touch screen. User interface 302 may be configured to display any information related to the delivery of stimulation therapy, identified patient behaviors, sensed patient parameter values, patient behavior criteria, or any other such information. User interface 302 may also receive user input via user interface 302. The input may be, for example, in the form of pressing a button on a keypad or selecting an icon from a touch screen.

Telemetry module 308 may support wireless communication between IMD 106 and programmer 104 under the control of processor 310. Telemetry module 308 may also be configured to communicate with another computing device via wireless communication techniques, or direct communication through a wired connection. In some examples, telemetry module 308 provides wireless communication via an RF or proximal inductive medium. In some examples, telemetry module 308 includes an antenna, which may take on a variety of forms, such as an internal or external antenna. In some examples, IMD 106 and/or programmer 104 may communicate with remote servers via one or more cloud-services in order to deliver and/or receive information between a clinic and/or programmer.

Examples of local wireless communication techniques that may be employed to facilitate communication between programmer 104 and IMD 106 include RF communication according to the 802.11 or Bluetooth specification sets or other standard or proprietary telemetry protocols. In this manner, other external devices may be capable of communicating with programmer 104 without needing to establish a secure wireless connection. As described herein, telemetry module 308 may be configured to transmit a spatial electrode movement pattern or other stimulation parameter values to IMD 106 for delivery of stimulation therapy.

According to the techniques of the disclosure, in some examples, processor 310 of external programmer 104 defines the parameters of a homeostatic therapeutic window, stored in memory 311, for delivering DBS to patient 112. In one example, processor 311 of external programmer 104, via telemetry module 308, issues commands to IMD 106 causing IMD 106 to deliver electrical stimulation therapy via electrodes 116, 118 via leads 114.

FIGS. 4A and 4B are conceptual diagrams of example leads 400 and 410, respectively, with respective electrodes carried by the lead. As shown in FIGS. 4A and 4B, leads 400 and 410 are embodiments of leads 114 shown in FIG. 1. As shown in FIG. 2A, lead 400 includes four electrode levels 404 (includes levels 404A-404D) mounted at various lengths of lead housing 402. Lead 400 is inserted into through cranium 122 to a target position within brain 18.

Lead 400 is implanted within brain 120 at a location determined by the clinician to be near an anatomical region to be stimulated. Electrode levels 404A, 404B, 404C, and 404D are equally spaced along the axial length of lead housing 30 at different axial positions. Each electrode level 404 may have one, two, three, or more electrodes located at different angular positions around the circumference (e.g., around the perimeter) of lead housing 402. As shown in FIG. 4A, electrode level 404A and 404D include a single respective ring electrode, and electrode levels 404B and 404C each include three electrodes at different circumferential positions. This electrode pattern may be referred to as a 1-3-3-1 lead in reference to the number of electrodes from the proximal end to the distal end of lead 400. Electrodes of one circumferential location may be lined up on an axis parallel to the longitudinal axis of lead 400. Alternatively, electrodes of different electrode levels may be staggered around the circumference of lead housing 402. In addition, lead 400 or 410 may include asymmetrical electrode locations around the circumference, or perimeter, of each lead or electrodes of the same level that have different sizes. These electrodes may include semi-circular electrodes that may or may not be circumferentially aligned between electrode levels.

Lead housing 402 may include a radiopaque stripe (not shown) along the outside of the lead housing. The radiopaque stripe corresponds to a certain circumferential location that allows lead 400 to the imaged when implanted in patient 112. Using the images of patient 112, the clinician can use the radiopaque stripe as a marker for the exact orientation of lead 400 within the brain of patient 112. Orientation of lead 400 may be needed to easily program the stimulation parameters by generating the correct electrode configuration to match the stimulation field defined by the clinician. In other embodiments, a marking mechanism other than a radiopaque stripe may be used to identify the orientation of lead 400. These marking mechanisms may include something similar to a tab, detent, or other structure on the outside of lead housing 402. In some embodiments, the clinician may note the position of markings along a lead wire during implantation to determine the orientation of lead 400 within patient 112. In some examples, programmer 104 may update the orientation of lead 400 in visualizations based on the movement of lead 400 from sensed signals.

FIG. 4B illustrates lead 410 that includes multiple electrodes at different respective circumferential positions at each of levels 414A-414D. Similar to lead 400, lead 410 is inserted through a burr hole in cranium 122 to a target location within brain 120. Lead 410 includes lead housing 412. Four electrode levels 414 (414A-414D) are located at the distal end of lead 410. Each electrode level 414 is evenly spaced from the adjacent electrode level and includes two or more electrodes. In one embodiment, each electrode level 414 includes three, four, or more electrodes distributed around the circumference of lead housing 412. Therefore, lead 410 includes 414 electrodes in a preferred embodiment. Each electrode may be substantially rectangular in shape. Alternatively, the individual electrodes may have alternative shapes, e.g., circular, oval, triangular, rounded rectangles, or the like.

In alternative embodiments, electrode levels 404 or 414 are not evenly spaced along the longitudinal axis of the respective leads 400 and 410. For example, electrode levels 404C and 404D may be spaced approximately 3 millimeters (mm) apart while electrodes 404A and 404B are 10 mm apart. Variable spaced electrode levels may be useful in reaching target anatomical regions deep within brain 120 while avoiding potentially undesirable anatomical regions. Further, the electrodes in adjacent levels need not be aligned in the direction as the longitudinal axis of the lead, and instead may be oriented diagonally with respect to the longitudinal axis.

Leads 400 and 410 are substantially rigid to prevent the implanted lead from varying from the expected lead shape. Leads 400 or 410 may be substantially cylindrical in shape. In other embodiments, leads 400 or 410 may be shaped differently than a cylinder. For example, the leads may include one or more curves to reach target anatomical regions of brain 18. In some embodiments, leads 400 or 410 may be similar to a flat paddle lead or a conformable lead shaped for patient 12. Also, in other embodiments, leads 400 and 410 may any of a variety of different polygonal cross sections (e.g., triangle, square, rectangle, octagonal, etc.) taken transverse to the longitudinal axis of the lead.

As shown in the example of lead 400, the plurality of electrodes of lead 400 includes a first set of three electrodes disposed at different respective positions around the longitudinal axis of the lead and at a first longitudinal position along the lead (e.g., electrode level 404B), a second set of three electrodes disposed at a second longitudinal position along the lead different than the first longitudinal position (e.g., electrode level 404C), and at least one ring electrode disposed at a third longitudinal position along the lead different than the first longitudinal position and the second longitudinal position (e.g., electrode level 404A and/or electrode level 404D). In some examples, electrode level 404D may be a bullet tip or cone shaped electrode that covers the distal end of lead 402.

Figure 5A:
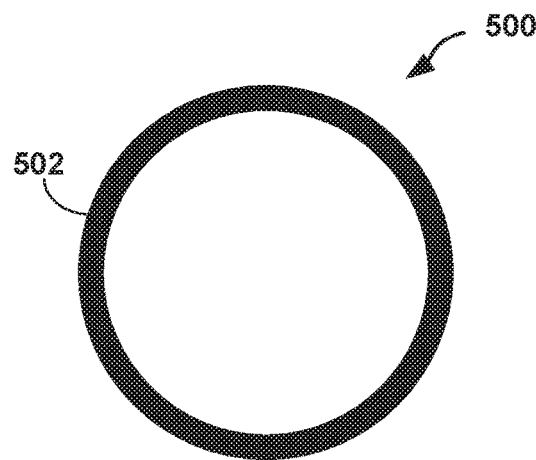
FIGS. 5A, 5B, 5C, and 5D are conceptual diagrams of example electrodes disposed around a perimeter of a lead at a particular longitudinal location.

FIGS. 5A-5D are transverse cross-sections of example stimulation leads having one or more electrodes around the circumference of the lead. As shown in FIGS. 5A-5D, one electrode level, such as one of electrode levels 404 and 414 of leads 400 and 410, are illustrated to show electrode placement around the perimeter, or around the longitudinal axis, of the lead. FIG. 5A shows electrode level 500 that includes circumferential electrode 502. Circumferential electrode 502 encircles the entire circumference of electrode level 500 and may be referred to as a ring electrode in some examples. Circumferential electrode 502 may be utilized as a cathode or anode as configured by the user interface.

Figure 5B:
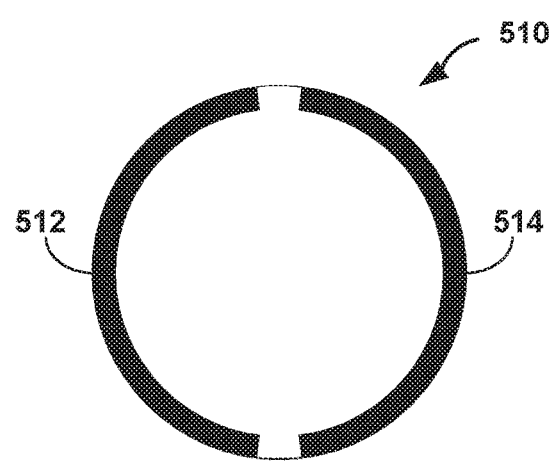

FIG. 5B shows electrode level 510 which includes two electrodes 512 and 514. Each electrode 512 and 514 wraps approximately 170 degrees around the circumference of electrode level 510. Spaces of approximately 10 degrees are located between electrodes 512 and 514 to prevent inadvertent coupling of electrical current between the electrodes. Smaller or larger spaces between electrodes (e.g., between 10 degrees and 30 degrees) may be provided in other examples. Each electrode 512 and 514 may be programmed to act as an anode or cathode.

Figure 5C:
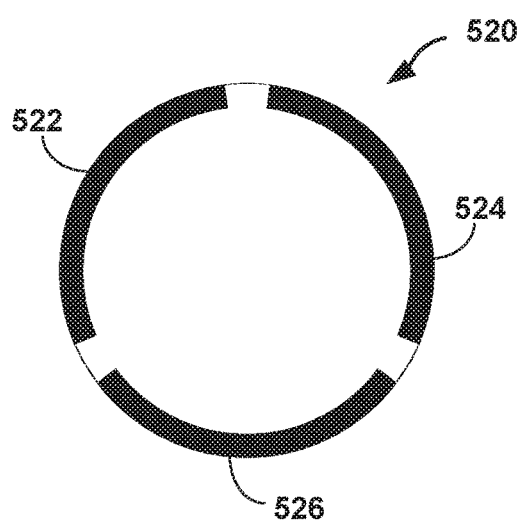

FIG. 5C shows electrode level 520 which includes three equally sized electrodes 522, 524 and 526. Each electrode 522, 524 and 526 encompass approximately 110 degrees of the circumference of electrode level 520. Similar to electrode level 510, spaces of approximately 10 degrees separate electrodes 522, 524 and 526. Smaller or larger spaces between electrodes (e.g., between 10 degrees and 30 degrees) may be provided in other examples. Electrodes 522, 524 and 526 may be independently programmed as an anode or cathode for stimulation.

Figure 5D:
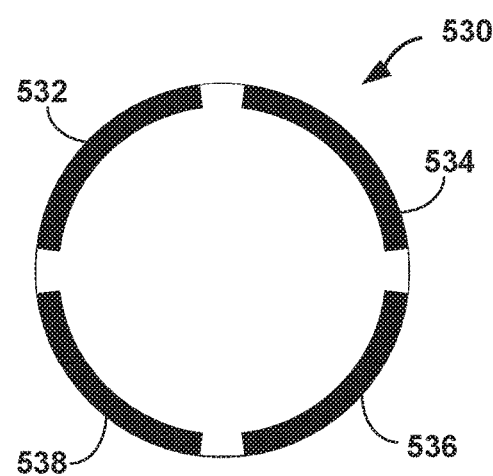

FIG. 5D shows electrode level 530 which includes four electrodes 532, 534, 536 and 538. Each electrode 532, 534, 536 and 538 covers approximately 80 degrees of the circumference with approximately 10 degrees of insulation space between adjacent electrodes. Smaller or larger spaces between electrodes (e.g., between 10 degrees and 30 degrees) may be provided in other examples. In other embodiments, up to ten or more electrodes may be included within an electrode level. In alternative embodiments, consecutive electrode levels of lead 114 may include a variety of electrode levels 500, 510, 520, and 530. For example, lead 114 (or any other lead described herein) may include electrode levels that alternate between electrode levels 510 and 530 depicted in FIGS. 5B and 5D. In this manner, various stimulation field shapes may be produced within brain 120 of patient 112. Further the above-described sizes of electrodes within an electrode level are merely examples, and the invention is not limited to the example electrode sizes.

Also, the insulation space, or non-electrode surface area, may be of any size. Generally, the insulation space is between approximately 1 degree and approximately 20 degrees. More specifically, the insulation space may be between approximately 5 and approximately 15 degrees. In other examples, insulation space may be between approximately 10 degrees and 30 degrees or larger. Smaller insulation spaces may allow a greater volume of tissue to be stimulated. In alternative embodiments, electrode size may be varied around the circumference of an electrode level. In addition, insulation spaces may vary in size as well. Such asymmetrical electrode levels may be used in leads implanted at tissues needing certain shaped stimulation fields.

Figure 6:
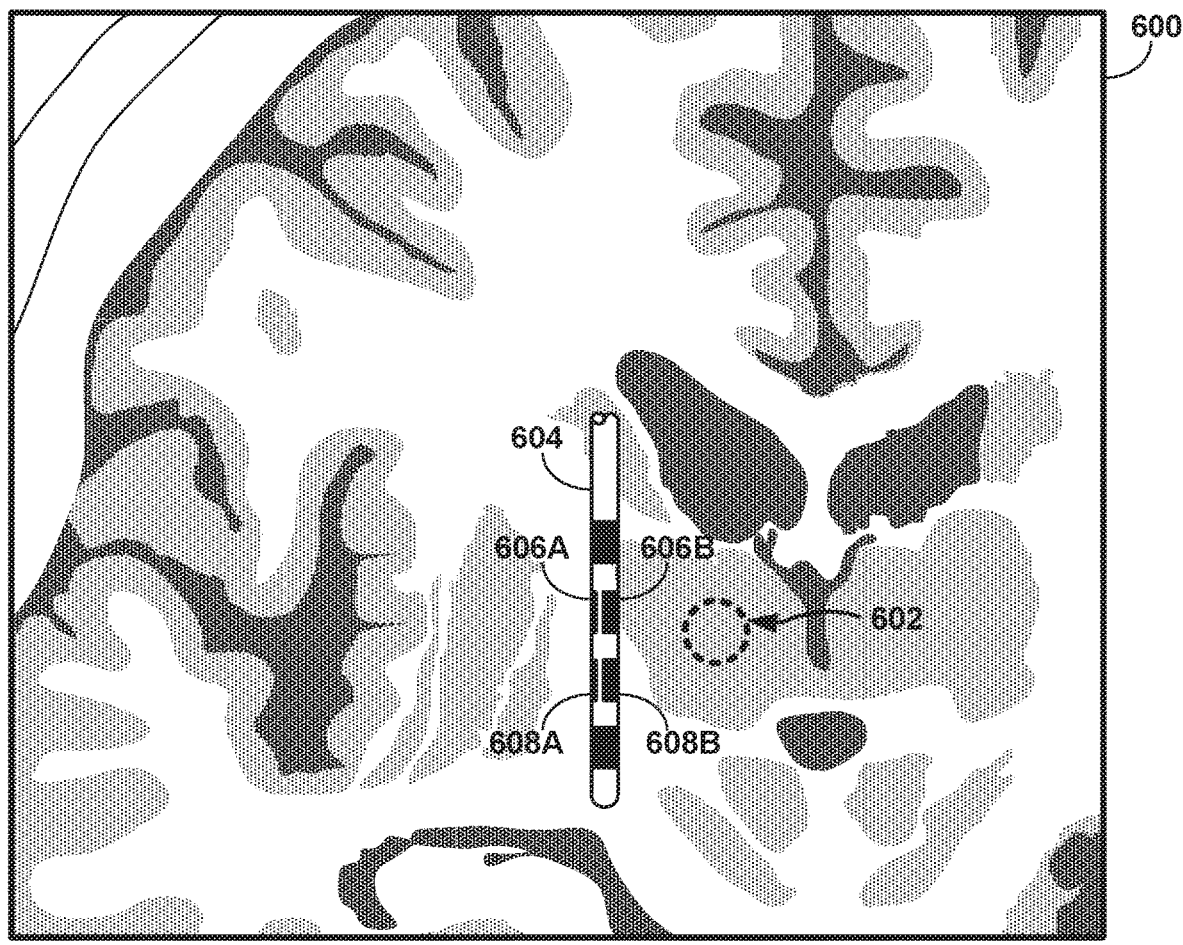
FIG. 6 is a coronal view of example tissue with a lead placed with respect to a target location within tissue.

FIG. 6 is a coronal view of example tissue with a lead 604 placed with respect to a target location within tissue. As shown in FIG. 6, a representation of anatomical regions of brain 120 is displayed by coronal view 600. Coronal view 600 is a front-back vertical section of brain 120. Coronal view 600 may be an actual image of brain 120 produced with magnetic resonance imaging (MRI), computed tomography (CT), or another imaging modality. Coronal view 600 may be an illustration of the location of a lead with respect to a target tissue from which electrical signals originate (e.g., LFP signals). In some examples, coronal view 600 may be presented by programmer 104 or another device to indicate the relative position of lead 604 and the electrodes carried by the lead according to the sensed electrical signals. These images thus may be used to produce the anatomical regions needed to help the clinician program the stimulation parameters.

Coronal view 600 is a 2D coronal slice of brain 120. Differently shaded portions of coronal view 92 indicate varying densities of tissue within brain 120. Darker portions indicate less dense tissue. For example, the darkest portion of coronal view 600 is indicative of spaces within brain 120 that contain cerebral spinal fluid (CSF). White portions of brain 120 indicate dense tissue and more neurons. It should be noted that coronal view 600 is only an example, and actual images may include a wider range of shades and higher image resolution. Coronal view 600 provides a first perspective of the lead and the anatomical region in which the lead is implanted.

As shown in FIG. 6, lead 604 may be a lead icon that represents an actual lead implanted within patient 112. Lead 604 includes electrodes such as electrodes 606A and 606B located at the same longitudinal position and different circumferential positions around the perimeter of lead 604. Electrode 606C cannot be seen because it is located in the backside of lead 604. Similarly, lead 604 includes electrodes such as electrodes 608A and 608B located at the same longitudinal position and different circumferential positions around the perimeter of lead 604. Electrode 608C cannot be seen because it is located in the backside of lead 604. When electrical signals, such as LFP signals originate from target tissue 602, the largest amplitude and power of the signal will likely be sensed by the electrode or electrodes closest to target tissue 602. In this example, a sensing electrode combination of electrodes 606B and 608B may sense a larger amplitude electrical signal from target tissue 602 than any other electrode combinations on lead 604. In some examples, monopolar sensing may result in electrode 606B sensing the highest amplitude of electrical signals from target tissue 602. If lead 604 moves with respect to tissue, a different electrode, such as electrode 606A (for lead rotation) or electrode 608B (for longitudinal lead movement), may not sense electrical signals with the largest amplitude.

Figure 7:
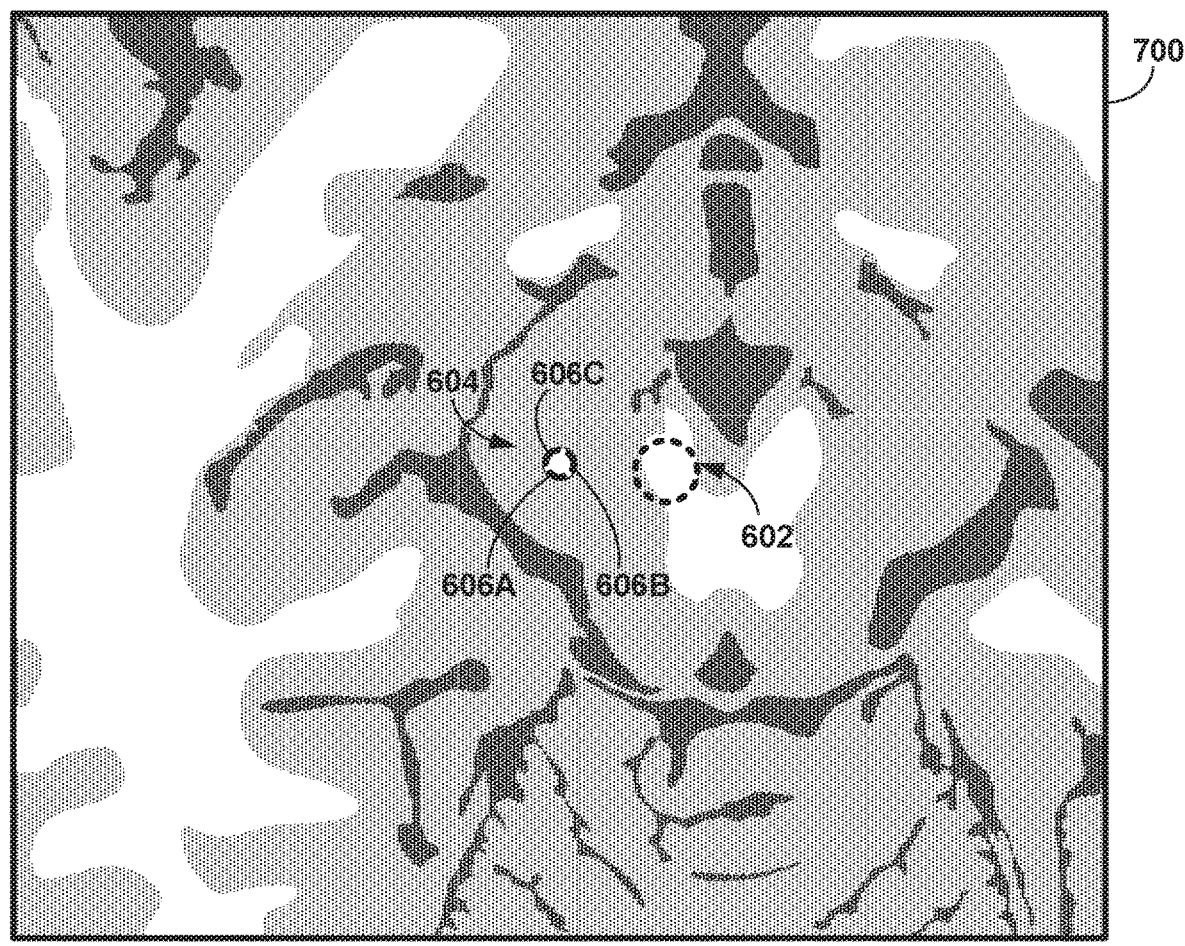
FIG. 7 is an axial view of example tissue with a lead placed with respect to a target location within tissue.

FIG. 7 is an axial view of example tissue with a lead 604 placed with respect to a target tissue 602. Axial view 700 is a different view of tissue than coronal view 600. Axial view 700 also shows the cross-sectional view of lead 604 and electrodes 606A, 606B, and 606C. As shown in axial view 700, electrode 606B is closest to target tissue 602 and may register the largest amplitude of sensed electrical signals when compared to the remaining electrodes of lead 604. If lead 604 were to rotate within tissue due to patient movement, lead pull, or some other force, a different electrode, such as electrode 606A, may be located closest to target tissue 602 and sense electrical signals with the largest amplitude when compared to other electrodes. Lead 604 may rotate due to other factors as well, such as infection, subdural hematoma, stroke, seizure, post-implant tissue swelling, inflammation, relaxation of frictional sheer-forces between tissue and lead, changes in polymer properties, residual coiling forces in lead wiring, or any other causes. Although FIGS. 6 and 7 discuss electrical signals that may originate in tissue, the same spatial origin may be used when sensing electrical signals evoked from delivered stimulation or sensing delivered stimulation itself for determining lead movement.

Figure 8A:
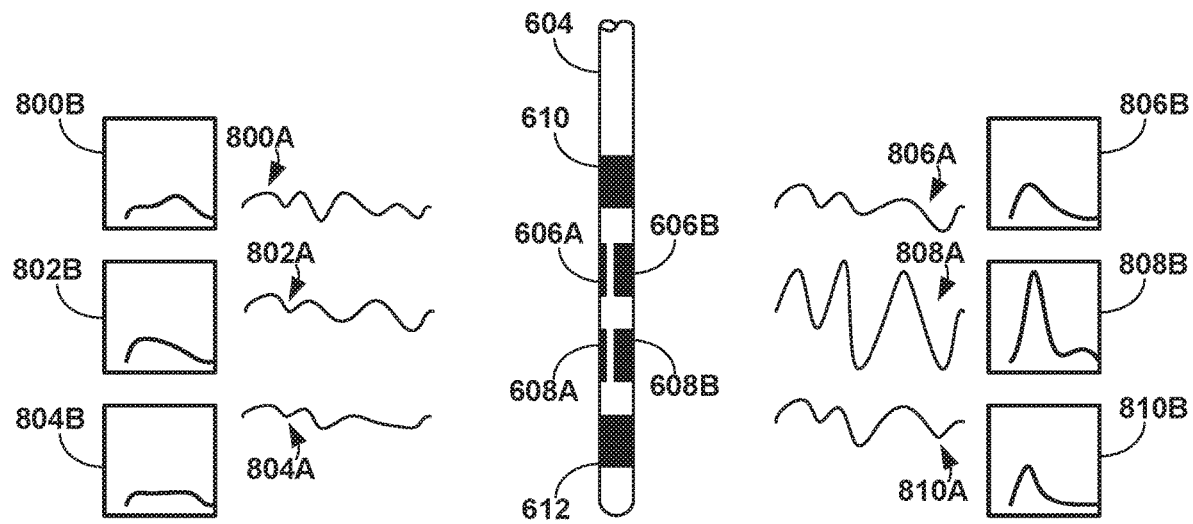
FIGS. 8A, 8B, 8C, and 8D are conceptual views of an example lead with example initial information and signal information recorded from respective electrode combinations.

FIGS. 8A, 8B, 8C, and 8D are conceptual views of an example lead 604 with example initial information and signal information recorded from respective electrode combinations. As shown in FIG. 8A, initial information may represent electrical signals sensed at a first time when lead 604 is in a first position with respect to tissue. The initial information may include one or more characteristics of the sensed electrical signals at the first time. The one or more characteristics may include some aspect of the electrical signals that can be used to compare the electrodes to each other over time. For example, the characteristic may be an amplitude of the sensed signal (e.g., absolute amplitude, a normalized amplitude, a categorized amplitude (e.g., amplitude values fall within separate predetermined ranges), or a ranked amplitude). This amplitude may be the maximum amplitude over a period of time, for example. In other examples, the characteristic may be a differential signal between electrodes or a spatial derivative (e.g., first or second spatial derivative) in the axial and/or angular directions to estimate the proximity of each electrode to a signal source. For example, the second spatial derivative may provide information regarding how fast the signal amplitudes change to provide an indication of proximity of that electrode or electrode combination to the signal source. In other examples, a full two dimensional or three dimensional Laplacian can be employed for simultaneous recording across electrodes for the characteristic of each electrode and compared over time to estimate movements of lead 604 in all directions (e.g., rotational and shifting movements).

In some examples, the characteristic may be a relative phase between electrodes. The relative phase may differentiate between multiple tissue signal sources that may be out of phase with each other. IMD 106 may thus analyze the relative phase for each electrode or electrode combination and determine the orientation of the electrode(s) with respect to the signal source or sources. The relative phase may be employed by IMD 106 to improve the confidence in the lead orientation or lead movement determination in some examples. In other examples, the characteristic may be a spectral power. The spectral power may be a power (e.g., absolute or normalized amplitude) for one or more frequency bands of the electrical signal. For example, IMD 106 may calculate the power of the beta frequency band for each sensed electrical signal, which may indicate the proximity of each electrode combination to a target neural location expected to generate signals in the beta frequency band. IMD 106 may select the frequency bad as generic for all patients or patient specific sensed signals. For example, the patient-specific frequency band may be selected to have a window centered around an identified peak in the spectrum (e.g., plus and minus 5 Hz from the identified peak). In other examples, IMD 106 may determine a rank for each electrode or electrode combination for any of the above-referenced parameters to determine if the rank of the electrodes changes between measurements. In this manner, the initial information (and signal information) may include determined characteristics representative of one or more aspects of the sensed electrical signals. In addition, or alternatively, the initial information (and signal information) may include at least a portion of the sensed electrical signal waveform for comparison to a template, threshold, or some other function enabling comparison of the electrical signals sensed by different electrode combinations. Any of these characteristics may be used alone or in combination with other characteristics to identify electrode position with respect to a signal source and/or lead movement over time. In addition, any of these characteristics may be employed by IMD 106 to determine x, y, and z or r, theta, and z coordinates, depending on the desired coordinate system, of the signal source. IMD 106 may then determine the coordinates of the signal source at multiple different times to identify any changes to the coordinates representative of lead movement (e.g., shift or rotation). In some examples, IMD 106 may perform corrections to sensed signals or include circuitry that balances impedance difference between electrodes of different sizes. This differences in impedances may alter the sensed signals and distort the determined distances to the signal source. IMD 106 may also compute corrections for different spacing between electrodes of different electrode combinations. For example, larger distances between electrodes similarly increases the amplitude of the sensed voltage. In order to compare signals from one electrode combination to another electrode combination with different spacing, IMD 106 may correct (or normalize) the sensed signal amplitude to compensate for these different spacings.

As shown in the example of FIG. 8A, waveform amplitudes 800A, 802A, 804A, 806A, 808A, and 810A (collectively "waveform amplitudes") are examples of initial information. Spectral powers 800B, 802B, 804B, 806B, 808B, and 810B (collectively "spectral powers") are additional, or alternative, examples of initial information. Each of the waveform amplitudes and spectral powers are determined from electrical signals sensed by a respective electrode combination. In the position of lead 604 as shown in the example of FIG. 8A, electrodes 606B and 608B are located on one side of lead 604 to detect signals such as waveform amplitudes 806A, 808A, and 810A and spectral powers 806B, 808B, and 810B. Conversely, electrodes 606A and 608A are located on a different side of lead 604 to detect signals such as waveform amplitudes 800A, 802A, and 804A and spectral powers 800B, 802B, and 804B. IMD 106 or another device may generate each of the spectral powers by analyzing the power of the frequencies present in the respective waveform amplitudes (e.g., spectral power 800B is generated by waveform amplitude 800A).

Each of the signals shown in FIG. 8A can be attributed to the signal sensed between an electrode combination of two electrodes. For example, IMD 106 may generate waveform amplitude 800A and/or spectral power 800B based on the electrical signal sensed between electrodes 610 and 606A. Similarly, IMD 106 may generate waveform amplitude 802A and/or spectral power 802B based on the electrical signal sensed between electrodes 606A and 608A and generate waveform amplitude 804A and/or spectral power 804B based on the electrical signal sensed between electrodes 608A and 612. Since electrodes 606A or 608A are part of the electrode combinations used to generate these signals, IMD 106 can determine that those signals originate from tissue in the direction of electrodes 606A or 608A. The same is true for other electrodes located at different positions around the perimeter of lead 604, such as electrodes 606B and 608B. Electrodes 606C and 608C are on the backside of lead 604 and cannot be viewed in the example of FIG. 8A. Therefore, IMD 106 may generate waveform amplitude 806A and/or spectral power 806B based on the electrical signal sensed between electrodes 610 and 606B. Similarly, IMD 106 may generate waveform amplitude 808A and/or spectral power 808B based on the electrical signal sensed between electrodes 606B and 608B and generate waveform amplitude 810A and/or spectral power 810B based on the electrical signal sensed between electrodes 608B and 612.

IMD 106 may monitor the signals sensed by the different electrode combinations over time to determine when the sensed signals, or characteristics of those signals, has changed indicating that lead 604 has rotated about the longitudinal axis and/or shifted along the longitudinal axis. For example, the largest waveform amplitude and the largest spectral power as shown in FIG. 8A was waveform amplitude 808A and spectral power 808B from the signals sensed by the electrode combination of electrodes 606B and 608B. This larger amplitude may indicate that the tissue of interest is closest to electrodes 606B and 608B than any other electrodes of lead 604. In other examples, there may not be a tissue of interest. Instead, IMD 106 may use one or more of the characteristics of the signals sensed by the respective electrode combinations to establish a baseline pattern of signals that indicates an initial position in tissue of lead 604. IMD 106 may use this initial baseline pattern to detect changes in the signals sensed from one or more electrode combinations indicative of electrode movement with respect to tissue.

Figure 8B:
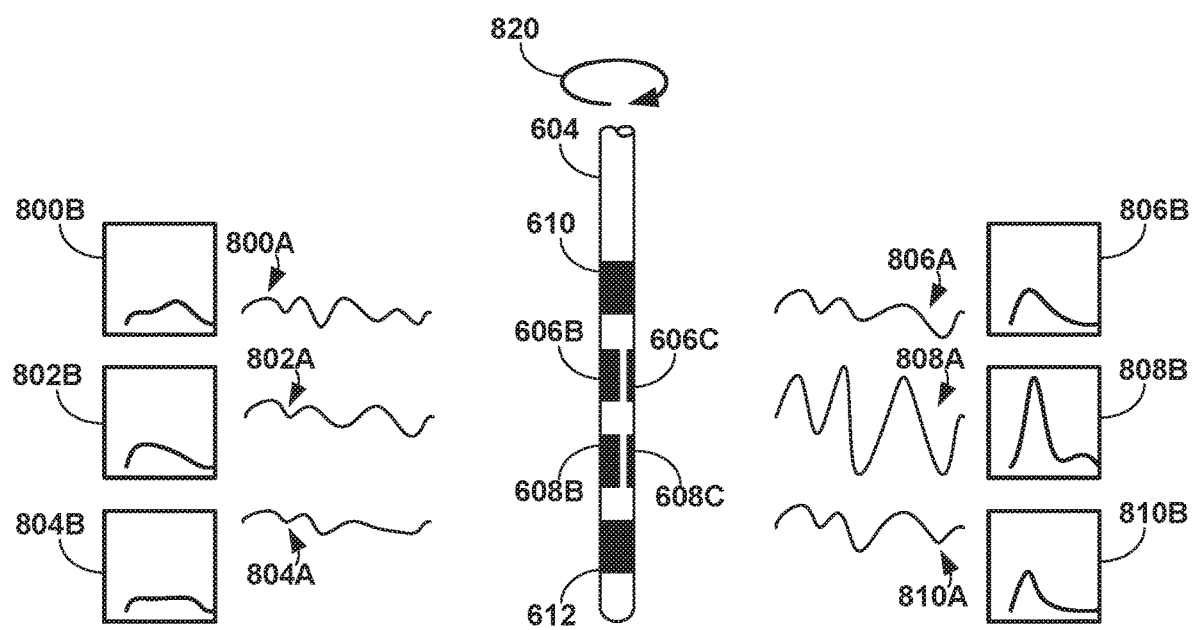

As shown in FIG. 8B, lead 604 has rotated in the direction of arrow 820 such that the electrode combinations of lead 604 sense different electrical signals in the new position of FIG. 8B than in the example of FIG. 8A. For example, IMD 106 may generate waveform amplitude 800A and/or spectral power 800B based on the electrical signal sensed between electrodes 610 and 606B. Similarly, IMD 106 may generate waveform amplitude 802A and/or spectral power 802B based on the electrical signal sensed between electrodes 606B and 608B and generate waveform amplitude 804A and/or spectral power 804B based on the electrical signal sensed between electrodes 608B and 612. Likewise, IMD 106 may generate waveform amplitude 806A and/or spectral power 806B based on the electrical signal sensed between electrodes 610 and 606B, generate waveform amplitude 808A and/or spectral power 808B based on the electrical signal sensed between electrodes 606C and 608C, and generate waveform amplitude 810A and/or spectral power 810B based on the electrical signal sensed between electrodes 608C and 612. IMD 106 may thus identify that the largest amplitude of waveform amplitude 808A or spectral power 808B is now associated with the electrode combination of electrodes 606C and 608C instead of by electrodes 606B and 608B. IMD 106 may thus identify that lead 604 has rotated in the direction of arrow 820. IMD 106 may thus adjust electrode combinations used to deliver therapy, adjust other therapy parameter values, initiate a reprogramming of therapy parameters, turn off therapy, or initiate an alert in response to determining that lead 604 has rotated with respect to tissue.

Although the same waveform amplitudes and spectral powers are shown in FIGS. 8A and 8B for illustrative purposes, the waveform amplitudes, spectral powers, or other characteristics of sensed electrical signals may be different between different electrode combinations as a result of lead movement. For example, after lead 604 rotates, electrodes 606C and 608C may not sense the same electrical signals as sensed by electrodes 606B and 608B prior to the rotation. However, IMD 106 may track the electrode combination that senses the largest waveform amplitude or spectral power, or a pattern of amplitudes, or identify when lead 604 has rotated.

IMD 106 may analyze any changes to the characteristics of electrical signals sensed by the electrode combinations to determine movement of lead 604 with respect to tissue in any direction. Using the techniques described herein, IMD 106 may determine that lead 604 rotated in tissue or shifted up or down along the longitudinal axis of lead 604. For example, IMD 106 may determine that the largest waveform amplitude is detected by the electrode combination of electrodes 608B and 612 instead of electrodes 606B and 608B to determine that lead 604 has shifted proximally. IMD 106 may continually monitor electrode signals over time to identify additional movements of lead 604, such as rotations or shifts of lead 604 with respect to tissue. IMD 106 may determine lead movements based on electrical signals sensed by electrodes on any array of electrodes, which may encompass, one, two, three, or more separate leads. In this manner, IMD 106 may monitor any group of electrode combinations to determine when the electrodes have moved with respect to tissue.

The example characteristics of the sensed electrical signals between electrodes of an electrode combination are the waveform amplitudes and spectral powers shown in FIGS. 8A and 8B. However, IMD 106 may determine lead rotation based on different characteristics of electrical signals. For example, IMD 106 may determine lead movement based on changes to impedances sensed for one or more electrode combinations. IMD 106 may sense impedance between at least two electrodes of respective electrode combinations. Since the sensed impedance is affected by tissue between the electrodes, IMD 106 may determine lead rotation based on changes to the sensed impedance of one or more electrode combinations.

Figure 8C:
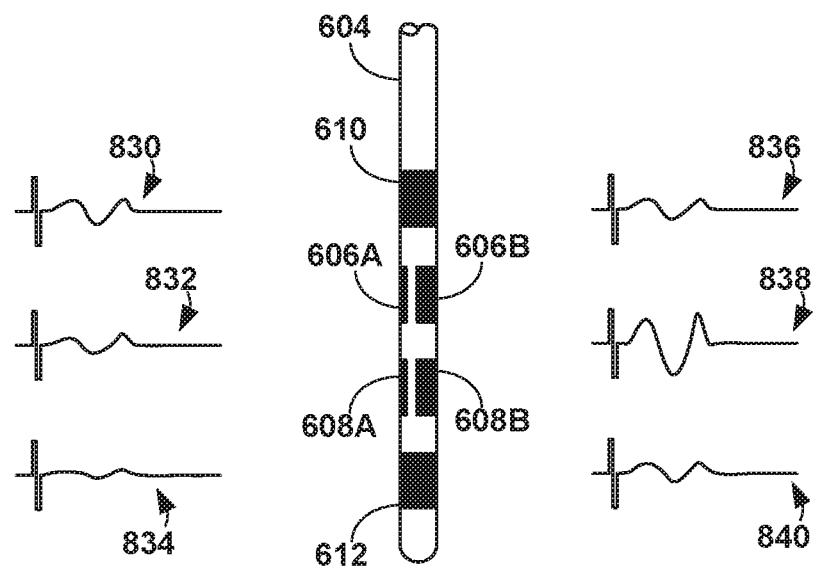

Other types of sensed signals or characteristics may be used by IMD 106 or another device to determine lead movement. As shown in FIG. 8C, IMD 106 may determine lead movement based on changes to sensed evoked responses (e.g., one or more characteristics of a physiologically generated electrical signal, such as an evoked compound action potential (ECAP)) sensed by one or more electrode combinations. IMD 106 may generate an electrical stimulus (e.g., a pulse or other waveform) via two or more electrodes on lead 604 or another lead. The electrical stimulus may be defined by stimulation parameters selected to elicit a nerve response that is detectable by electrodes on lead 604. The amplitude of the nerve response may be proportional to the distance from the stimulus electrodes and the nervous tissue and the distance from the nervous tissue and the sensing electrodes. Therefore, the amplitude of the sensed evoked signal may be indicative of how far the sensing electrodes are from the nervous tissue and whether or not the electrodes have moved with respect to the tissue. IMD 106 may sense evoked signals from all electrode combinations based on a single stimulus or sense evoked signals for each electrode combination from respective stimuli. IMD 106 may sense the evoked response on the same lead or a different lead than the lead which delivered the stimulation that elicited the evoked response. When stimulation is delivered by electrodes on one lead and evoked signals are sensed by electrodes on another lead, IMD 106 may determine from the sensed evoked signals whether the stimulation lead or the sensing lead has moved with respect to tissue.

For example, IMD 106 may generate waveform signal 830 based on the electrical signal sensed between electrodes 610 and 606A as a result of the delivered stimulus. Each sensed waveform signal, such as waveform signal 830, may include a first biphasic square wave pulse (e.g., an artifact representing the delivered stimulus) followed by the evoked signal from stimulated neural tissue. Similarly, IMD 106 may generate waveform signal 832 based on the electrical signal sensed between electrodes 606A and 608A and generate waveform signal 834 based on the electrical signal sensed between electrodes 608A and 612. Likewise, IMD 106 may generate waveform signal 836 based on the electrical signal sensed between electrodes 610 and 606B, generate waveform signal 838 based on the electrical signal sensed between electrodes 606B and 608B, and generate waveform signal 840 based on the electrical signal sensed between electrodes 608B and 612.

IMD 106 may analyze the amplitude, area under the curve, or other characteristic of at least a portion of the evoked waveform following the artifact. For example, the sensed signal may include multiple peaks of alternating polarities, and IMD 106 may analyze one or more of any of the peaks of the sensed signal. Similar to the waveform amplitude or spectral power discussed above, IMD 106 may monitor for changes to the evoked waveform characteristic, such as amplitude, over time. If the lead has moved, the sensed evoked response will change for one or more electrode combinations because the distance between the stimulus electrode(s) and the evoked tissue and/or the distance between the sensing electrodes and the evoked tissue will have changed. For example, evoked waveform 838 has the largest amplitude as sensed by electrodes 606B and 608B. If IMD 106 then determines that the electrode combination of electrodes 606A and 608A senses an evoked waveform that has the largest amplitude of all electrode combinations, then IMD 106 may determine that lead 604 has rotated such that electrodes 606A and 608A are now closer to the neuronal tissue than electrodes 606B and 608B.

Figure 8D:
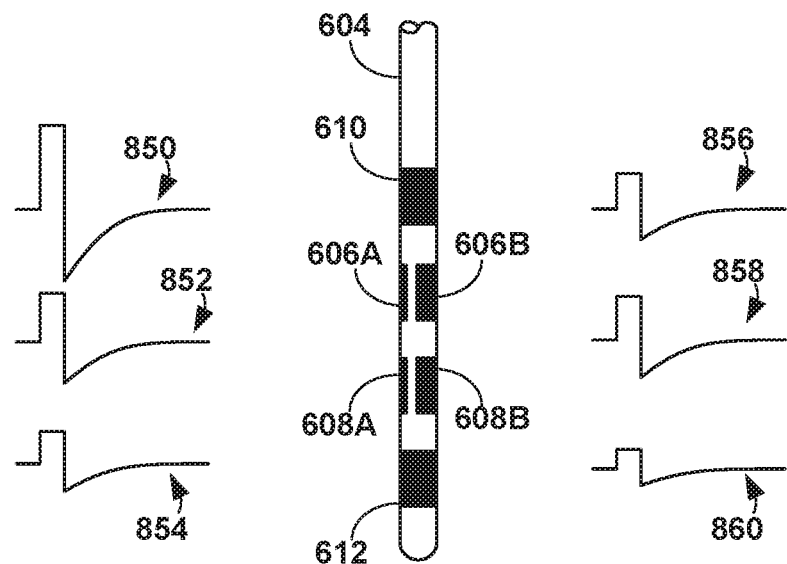

FIG. 8D illustrates another technique for determining lead movement that is similar to the evoked waveforms used in FIG. 8C. However, IMD 106 may determine lead movement based on changes to sensed electrical stimulus itself from one or more distant electrodes. IMD 106 may generate the electrical stimulus from an electrode on a housing of IMD 106, an electrode on a different lead, or control a different device (external or internal device) to deliver the electrical stimulus. IMD 106 may sense the electrical stimulus from one or more electrical combinations on lead 604, and this sensed signal may be referred to as an artifact or pulse because it is not physiological in origin. Nonetheless, electrodes closest to the origin of the electrical stimulus may sense the stimulus as a larger amplitude, indicative of the orientation of lead 604 with respect to the location of the electrical stimulus.

For example, IMD 106 may generate sensed signal 850 based on the electrical signal sensed between electrodes 610 and 606A indicative of the delivered stimulus. Each sensed signal, such as sensed signal 850, may include a first biphasic square wave pulse (e.g., an artifact representing the delivered stimulus). Similarly, IMD 106 may generate sensed signal 852 based on the electrical signal sensed between electrodes 606A and 608A and generate sensed signal 854 based on the electrical signal sensed between electrodes 608A and 612. Likewise, IMD 106 may generate sensed signal 856 based on the electrical signal sensed between electrodes 610 and 606B, generate sensed signal 858 based on the electrical signal sensed between electrodes 606B and 608B, and generate sensed signal 860 based on the electrical signal sensed between electrodes 608B and 612. In the example of FIG. 8D, the largest sensed amplitude may be from sensed signal 850 from electrodes 606A and 610. If subsequent sensed signals indicate that a different electrode combination senses a signal with the largest amplitude, then IMD 106 may determine that lead 604 has moved in accordance with the different electrode combination sensing the largest amplitude sensed signal.

In this manner, if IMD 106 or another device delivers an electrical stimulus from an electrode not part of lead 604, for example, the electrode combinations of lead 604 will sense that delivered electrical stimulus with different respective amplitudes based on the orientation of the electrodes of each electrode combination with respect to the stimulus electrode. If the lead has moved, the sensed stimulus amplitude will change for one or more electrode combinations because the distance between the stimulus electrode(s) and sensing electrodes of each electrode combination will have changed. IMD 106 may use any of these, or combinations of these, sensing techniques in order to determine movement of electrodes of a lead with respect to tissue.

In some examples, IMD 106, an external system (e.g., a lead trialing system), and/or a physician may implement the techniques described herein to intraoperatively rotate and/or shift the position of the lead to a target location with respect to surrounding anatomy. For example, the physician or surgical robot may rotate and/or shift the lead until an electrode, or electrode combination, is directly positioned to record the greatest signal indicative of the electrode being closest to the desired target tissue from which the sensed signal originates. This positioning during implantation may enable the physician to improve the available therapeutic window (e.g., the greatest difference in amplitude between the minimum amplitude that provides therapy and the maximum amplitude that elicits side effects). This positioning may also reduce the electrical current requires to provide effective therapy. To enable this intraoperative positioning technique, the lead may be connected to a trialing system similar to IMD 106, the IMD 106 itself, or an external recording system. If the lead is not directly connected to IMD 106, the physician may connect the lead to IMD 106 once positioned.

Figure 9A:
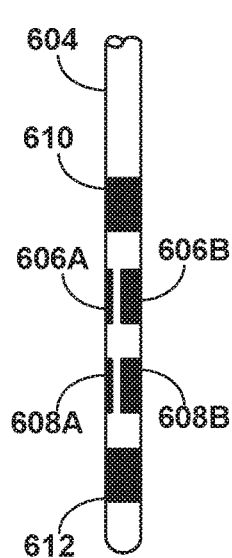
FIG. 9A is a conceptual view of an example lead.

FIG. 9A is a conceptual view of an example lead 604. Lead 604 is also shown in FIGS. 8A-8D, and includes a distal ring electrode 612 and a proximal ring electrode 610. Between these ring electrodes 610 and 612 is two axial levels of electrodes. The first axial level includes electrode 606A at a first circumferential position, electrode 606B at a second circumferential position different than the first circumferential position, and another electrode (electrode 606C not shown) at a third different circumferential position. Similarly, the second axial level that is at a more distal location along the longitudinal axis of lead 604 includes three electrodes at different circumferential positions. Electrode 608A is at a first circumferential position, electrode 608B is at a second circumferential position, and electrode 608C (not shown) is at a third circumferential position. Any of the electrodes of lead 604 may be used in an electrode combination to deliver an electrical stimulus and/or sense electrical signals. The eight electrodes of lead 604 is just one example electrode array. Other leads may have a different number of electrodes and/or combinations of ring electrodes and electrodes around the perimeter of the lead. For example, one or more axial levels of another lead may have two electrodes, four electrodes, or more electrodes at different positions around the perimeter of the lead. In some examples, a lead may include one or more different axial levels of electrodes at different locations around the perimeter of the lead without any ring electrodes. In some examples, the distal ring electrode, such as ring electrode 612, may be disposed at the very distal tip of lead 604 such that the electrode creates a bullet tip or cone electrode completely covering the distal end of the lead.

Figure 9B:
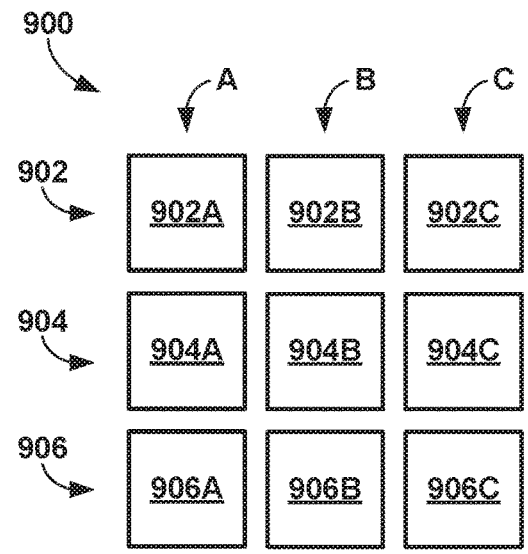
FIGS. 9B, 9C, 9D, 9E, 9F, 9G, and 9H are conceptual illustrations of example matrices representing electrical signals sensed by respective electrode combinations.

FIGS. 9B, 9C, 9D, 9E, 9F, 9G, and 9H are conceptual illustrations of example matrices representing electrical signals sensed by respective electrode combinations. Although the electrode array of lead 604 will be described herein as an example, the same techniques may be applied to any leads carrying multiple electrodes in any orientation, but the matrix of block may be of a different size. As shown in FIG. 9B, each of blocks 902A, 902B, 902C, 904A, 904B, 904C, 906A, 906B, and 906C (collectively "blocks 900") represents a single electrode combination. Rows and columns of blocks 900 represent electrode combinations at the same longitudinal position of the lead and the same circumferential position of the lead, respectively. For example, block 902A (row 902 and column A) represents the electrode combination of electrodes 610 and 606A of lead 604, block 902B (row 902 and column B) represents the electrode combination of electrodes 610 and 606B, and block 904B (row 904 and column B) represents the electrode combination of electrodes 606B and 608B. Once IMD 106 or other device determines the characteristics of the sensed electrical signals for each electrode combination, IMD 106 can place the characteristics in respective blocks of blocks 900 to create a matrix of characteristics for all of the electrode combinations.

Figure 9C:
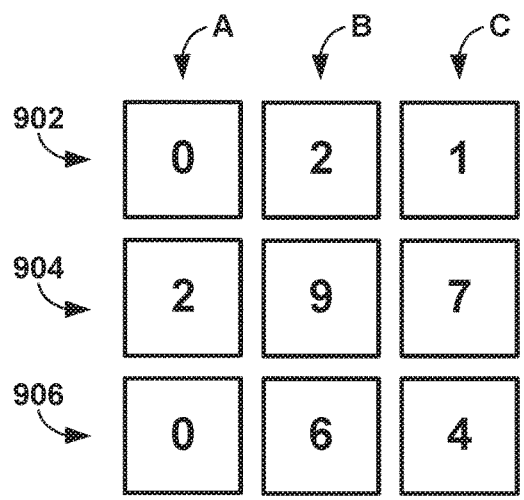
Figure 9D:
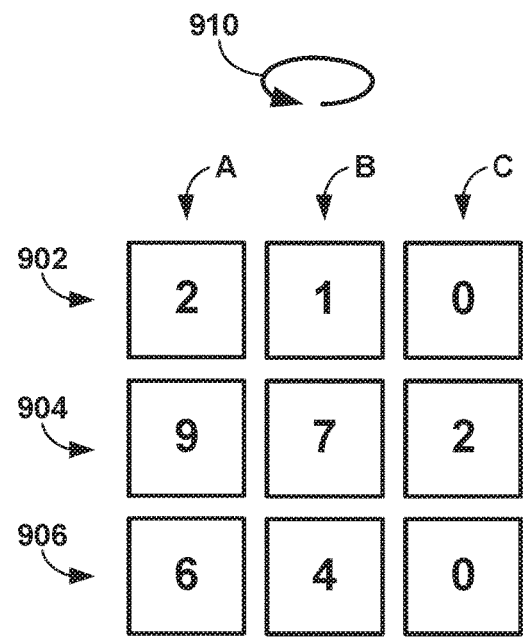

As shown in FIG. 9C, IMD 106 has created an initial matrix of characteristic values of the electrical signals sensed for respective electrode combinations. The characteristic values may be a normalized amplitude of the sensed signals, so a value of "9" in block 904B indicates a higher amplitude sensed signal than the value of "2" in block 902B. IMD 106 may monitor the characteristics for the same electrode combinations over time. If lead 604 rotates in the direction of arrow 910, as shown in FIG. 9D, IMD 106 may create a second matrix in which the characteristic values for the electrical signals sensed by respective electrode combinations may change. These characteristic values may indicate that the lead rotated.

For example, the highest characteristic value of "9" is now sensed by electrode combination 904A in FIG. 9D instead of electrode combination 904B in FIG. 9C. Using this change to the matrix, IMD 106 may determine that lead 604 has rotated such that electrodes 606A and 608A are now closest to the origin of the electrical signal sensed by the electrodes of lead 604. It is noted that in some examples the lead may not rotate to a complete next electrode position around the perimeter of the lead. Therefore, the characteristic values may be different altogether instead of just shifted to a different electrode combination. For example, instead of blocks 904A and 904B showing values of 9 and 7, respectively, in FIG. 9D, the lead may not rotate as much such that blocks 904A and 904B show values of 8 and 8, respectively. This similar amplitude would indicate that the origin of the electrical signal occurs between the circumferential positions of electrodes 606A and 606B.

Figure 9E:
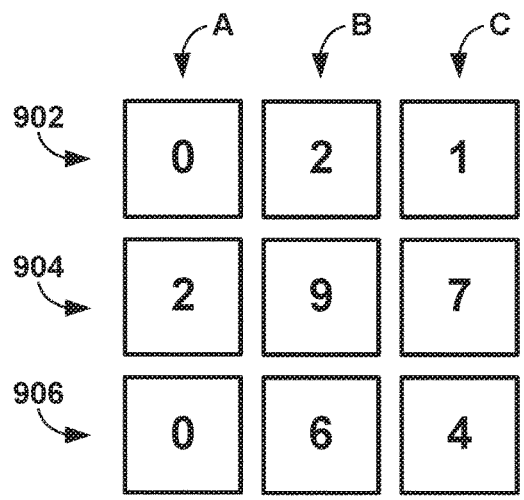
Figure 9F:
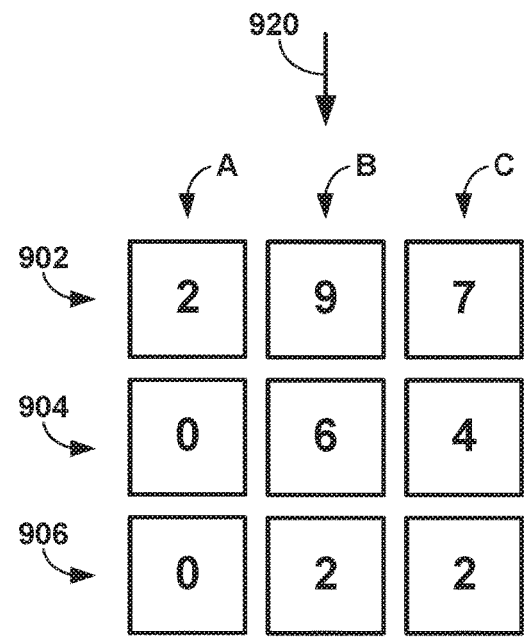

As shown in FIGS. 9E and 9F, lead shifting along a longitudinal direction of arrow 920 may cause the characteristic values of blocks 900 to shift proximally as different electrodes would then sense the stronger electrical signal. In FIG. 9E, block 904B includes the highest characteristic value of 9. However, after the shift the lead in the direction of arrow 920, block 902B in FIG. 9F now includes the highest characteristic value of 9 indicating that electrodes 610 and 606B are sensing the strongest electrical signals. Blocks 906A, 906B, and 906C include different characteristic values not included in FIG. 9E because the electrodes of those electrode combinations have moved to a new area of tissue.

Figure 9G:
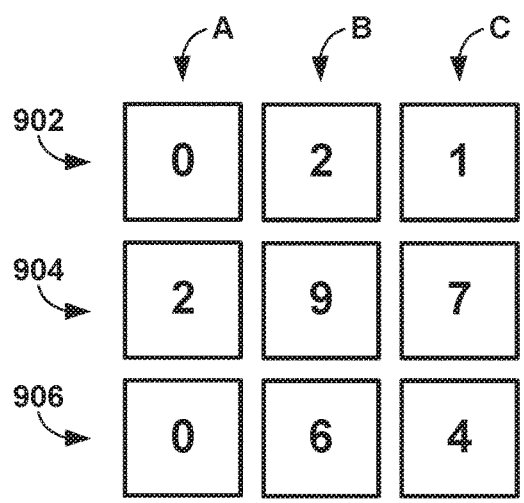
Figure 9H:
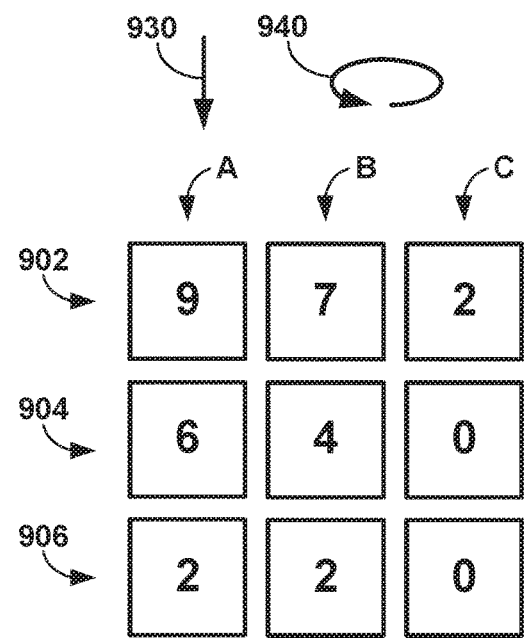

As shown in FIGS. 9G and 9H, lead shifting along a longitudinal direction of arrow 930 and rotation in the direction of arrow 940 may cause the characteristic values of blocks 900 to shift proximally and circumferentially as different electrodes would then sense the stronger electrical signal. In FIG. 9G, block 904B includes the highest characteristic value of 9. However, after the shift and rotation of the lead in the direction of arrows 930 and 940, respectively, block 902A in FIG. 9H now includes the highest characteristic value of 9 indicating that electrodes 610 and 606A are sensing the strongest electrical signals. Blocks 906A, 906B, and 906C include different characteristic values not included in FIG. 9G because the electrodes of those electrode combinations have moved to a new area of tissue.

As discussed above, the characteristic values are normalized, or scaled, to the largest amplitude of the electrical signals sensed by all of the electrode combinations. In some examples, the scaled values may be scaled to a percentage of the largest amplitude or scaled to any other arbitrary number. In this manner, the characteristic values may be "binned" or grouped according to the sensed amplitude or other characteristic. In other examples, the characteristic value may be the actual calculated amplitude of the sensed electrical signals. In other examples, IMD 106 may rank each electrode combination to the magnitude or other characteristic of the sensed electrical signals. Instead of an amplitude of the signal, other characteristics such as spectral power may be used in the matrix of other examples. Although the descriptions of FIGS. 9A-9H describe bipolar sensing, IMD 106 may conduct monopolar sensing by sensing between an electrode on lead 604 and another reference electrode carried by the housing of IMD 106 or other return electrode more proximal on the lead such as near the skull. In this manner, each of blocks 900 may only include the same number of blocks as number of electrodes on lead 604 for monopolar sensing.

IMD 106 may estimate the 2D or 3D position of the signal source with respect to one or more electrodes (or lead 604). For example, IMD 106 can detect a change in the matrix of blocks 900 (likely a low-power operation). IMD 106 can then determine that the change does not align with a vertical or horizontal shift in the signals from one matrix to the next matrix (e.g., a low-power operation). IMD 106 then signals the need for a source-location estimation, and does one of two next steps: (a) computes a new 2D or 3D source location of the target tissue or (b) sends sense data to an external device to compute intensive 2D or 3D source localization. IMD 106 may send the data directly to external device, send a message that a difference was detected to external device to initiate a request for sensing session data, or send a flag that is read by an external device to prompt a request for sensing session data to confirm rotation or shifting of the lead. Previous source localization may be stored on IMD 106, an external device, or at a remote server of a cloud service for comparison.

Figure 10:
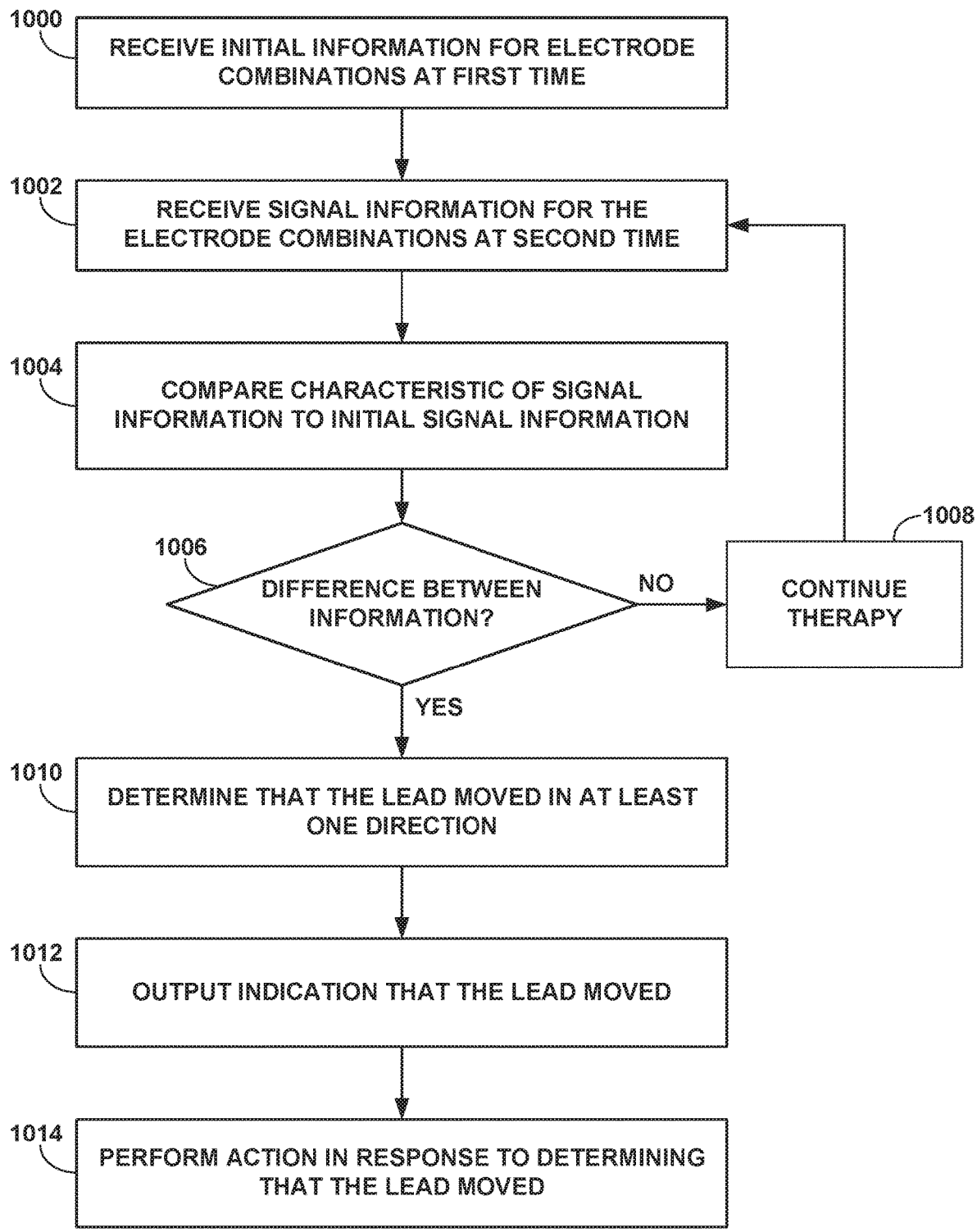
FIG. 10 is a flowchart illustrating an example technique for determining whether a lead has moved with respect to tissue.

FIG. 10 is a flowchart illustrating an example technique for determining whether a lead has moved with respect to tissue. The technique of FIG. 10 will be described with respect to processor 210 of IMD 106 in FIG. 2. However, other processors, devices, or combinations thereof, may perform the techniques of FIG. 10 in other examples.

As shown in FIG. 10, processor 210 receives initial information for electrode combinations at a first time (1000). The initial information may be raw signal information, filtered signal information, characteristic values of the signals sensed by the electrode combinations, or any other information representative of the sensed electrical signals. If processor 210 receives signal information, processor 210 may determine one or more characteristic values for the signal information for each electrode combination. Processor 210 may then receive signal information for the electrode combinations at a second time (1002). Generally, the second signal information may be for the same electrode combinations. However, in some examples, processor 210 may only receive signal information for a subset of the electrode combinations. If the second signal information does not include characteristic values, processor 210 may determine the characteristic values for the respective electrode combinations from the second signal information.

Processor 210 then compares the characteristic values from the second signal information to the characteristic values from the initial signal information (1004). If processor 210 determines that there is no difference between the characteristic values ("NO" branch of block 1006), then processor 210 continues to control the delivery of therapy (1008) and receives additional signal information (1002) to continue to monitor for any lead movement. When determining that the characteristic values are the same or different between different times, processor 210 may use a tolerance or deviation threshold such that the characteristic values do not need to be exactly the same for processor 210 to determine that there has been no movement to the electrodes. The tolerance or deviation threshold may be a percentage of previous values, probability that the lead has moved, or other such calculation that allows for some difference in characteristic values before processor 210 determines that the lead has moved.

If processor 210 determines that there is a difference between the characteristic values from sensed signals at different times ("YES" branch of block 1006), processor 210 then determines that the lead moved in at least one direction with respect to surrounding tissue (1010). In some examples, processor 210 may run one or more tests to determine that the identified lead movement is not attributed to a lead fracture, noise, or other hardware or sensing issue, prior to determining that the lead moved in step 1010. A test may include comparing the sensed signals to known operational ranges, lead impedances, signal entropy, frequency characteristics, known failure modalities, measured movement of the patient, or any other such measurements. These types of signal quality checks may be performed by processor 210 for any technique described herein when determining a signal or comparing sensed signals. In response to determining that the lead moved, processor 210 outputs an indication that the lead has moved (1012). This indication may be data stored in memory, a flag indicating that the lead movement was detected, or some other similar indication. Processor 210 then performs one or more actions in response to determining that the lead has moved (1014). In some examples, processor 210 may stop delivery of therapy in response until one or more parameter values are adjusted to accommodate the movement or a user confirms that therapy should continue.

Processor 210 may perform, or control another device to perform, one or more actions in response determining that the lead has moved. For example, processor 210 may transmit an alert to an external programmer, such as programmer 104, indicating that the lead has moved. Programmer 104 may then control a user interface to present a representation of the alert to the user. This alert may simply instruct the user that the lead has moved. However, the alert may provide more information. For example, the alert may indicate which direction the lead moved, whether the lead rotated or shifted longitudinally, or some other aspect of the movement. In some examples, the alert may include more specific information, such as characteristic values of the sensed electrical signals, the electrical signals themselves, or a representation of the matrix values or the shift to the matrix values. In this manner, programmer 104 or another device may present specific information regarding how the lead has moved within the patient. In addition, or alternatively, the alert may recommend that the user reprograms one or more therapy programs because the lead movement may render the old therapy programs ineffective. Processor 210 or programmer 104 may additionally, or alternatively, recommend changes to one or more stimulation parameters to accommodate the lead movement. Any of these alerts may indicate to the user that stimulation parameters need to be adjusted in order to reestablish effective therapy instead of a reduction in efficacy caused by degeneration of tissue. In other examples, processor 210 may test for lead movement in response to one or more trigger events. A trigger event may be one or more sensors determining that the stimulation therapy is less effective at reducing patient symptoms (e.g., one or more accelerometers detect increased instances or magnitude of tremor) or causes or increases side effects (e.g., detection of dyskinesia). In some examples, processor 210 may detect reduced therapeutic efficacy based on sensed brain signals (e.g., changes to a spectral power in one or more frequency bands). A trigger event may also be programmer 104 receiving patient input indicating that therapy is less effective or that the patient has fallen or endured some other event that may have caused lead movement.

In other examples, processor 210 may initiate an analysis of stimulation parameters in response to determining that the lead has moved. For example, processor 210 may change electrode combinations for delivery therapy according to the movement detected. In some examples, processor 210 may model electrical fields or other representations of therapy and adjust other parameters such as amplitude in order to recreate the therapy provided by the parameters used prior to the lead movement. These similar adjustments may be made to recording or sensing electrodes used to monitor physiological signals for the patient. In these or other manners, processor 210 may automatically adjust one or more stimulation parameters, such as electrode combinations or amplitude, for providing stimulation therapy or recording electrical signals after the lead has moved. In some examples, processor 210 may transmit the adjusted parameter values to an external device, such as programmer 104, for the user to confirm that the adjustments are appropriate. Processor 210 may then adjust the stimulation parameter values in response to receiving user confirmation from the external device.

As described herein, processor 210 may determine different types of characteristic values to represent whether or now leads have moved. Spectral power is one type of characteristic value. In one example, processor 210 may employ a logistic regression classifier to include spectral band power features and time domain threshold crossing statistic features. Processor 210 may initially filter the sensed brain signal, such as removing a first portion (e.g., 10 seconds) and a last portion (e.g., 2.5 seconds) to avoid transient signals. Processor 210 may determine spectral features by computing band power over several frequency intervals. In one example, these frequency bands may include 0-3 Hz, 3-5 Hz, 5-10 Hz, 10-20 Hz, 20-30 Hz, 40-50 Hz, 50-60 Hz, 70-80 Hz, and 80-90 Hz. Processor 210 may then normalize the power by dividing the power for each band by the total power calculated in the band from 0-90 Hz. Processing circuitry 310 may then compute the entropy of normalized band powers. In some examples, the entropy of normalized band powers will be summed for used by the logistic regression classifier. In this manner, the spectral power may be a representation of the spectral power in certain bands to represent the electrical signals sensed by each electrode combination.

Figure 11:
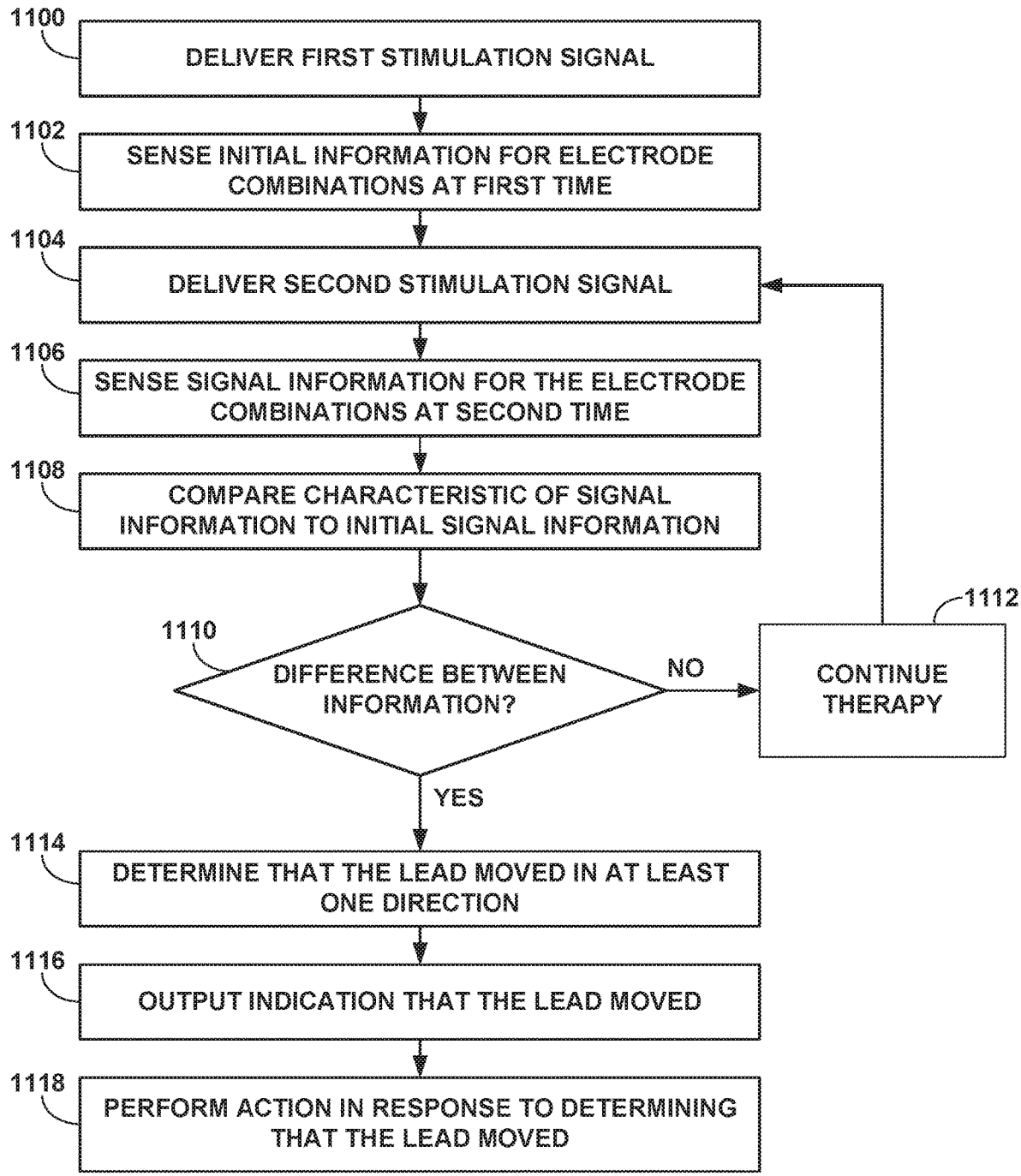
FIG. 11 is a flowchart illustrating an example technique for determining whether a lead has moved with respect to tissue.

FIG. 11 is a flowchart illustrating an example technique for determining whether a lead has moved with respect to tissue. FIG. 11 may be similar to the technique of FIG. 10, but the technique of FIG. 11 may utilize evoked signals to determine movement of a lead. The technique of FIG. 11 will be described with respect to processor 210 of IMD 106 in FIG. 2. However, other processors, devices, or combinations thereof, may perform the techniques of FIG. 11 in other examples.

As shown in FIG. 11, processor 210 delivers a first stimulation signal to tissue via an electrode combination (1100). Processor 210 then senses initial information for electrode combinations at a first time (1102). The initial information may be raw signal information, filtered signal information, or any other information sensed by the electrode combinations, or any other information representative of the sensed electrical signals. Processor 210 may determine one or more characteristic values for the signal information for each electrode combination. Processor 210 also delivers a second stimulation signal to tissue via the electrode combination (1104). The electrode combination may be the same electrode combination that delivered the first stimulation signal. In other examples, different stimulation signals may be delivered for sensing from respective electrode combinations. Processor 210 may then sense signal information for the electrode combinations at a second time (1006). Generally, the second signal information may be for the same electrode combinations. However, in some examples, processor 210 may only sense signal information for a subset of the electrode combinations. If the second signal information does not include characteristic values, processor 210 may determine the characteristic values for the respective electrode combinations from the second signal information. Processor 210 may evaluate the characteristics of the waveform of evoked signals (e.g., an ECAP signal) from tissue that was elicited by the delivered stimulation signals. In other examples, processor 210 may evaluate the characteristics of the sensed delivered stimulation signal, instead of signals from tissue, for determining the movement of a lead.

Processor 210 then compares the characteristic values from the second signal information to the characteristic values from the initial signal information (1008). If processor 210 determines that there is no difference between the characteristic values ("NO" branch of block 1010), then processor 210 continues to control the delivery of therapy (1112) and receives additional signal information (1004) to continue to monitor for any lead movement. When determining that the characteristic values are the same or different between different times, processor 210 may use a tolerance or deviation threshold such that the characteristic values do not need to be exactly the same for processor 210 to determine that there has been no movement to the electrodes. The tolerance or deviation threshold may be a percentage of previous values, probability that the lead has moved, or other such calculation that allows for some difference in characteristic values before processor 210 determines that the lead has moved.

If processor 210 determines that there is a difference between the characteristic values from sensed signals at different times ("YES" branch of block 1110), processor 210 then determines that the lead moved in at least one direction with respect to surrounding tissue (1114). In response to determining that the lead moved, processor 210 outputs an indication that the lead has moved (1116). This indication may be data stored in memory, a flag indicating that the lead movement was detected, or some other similar indication. Processor 210 then performs one or more actions in response to determining that the lead has moved (1118). In some examples, processor 210 may stop delivery of therapy in response until one or more parameter values are adjusted to accommodate the movement or a user confirms that therapy should continue. Processor 210 may take similar actions as discussed above with respect to FIG. 10.

Figure 12:
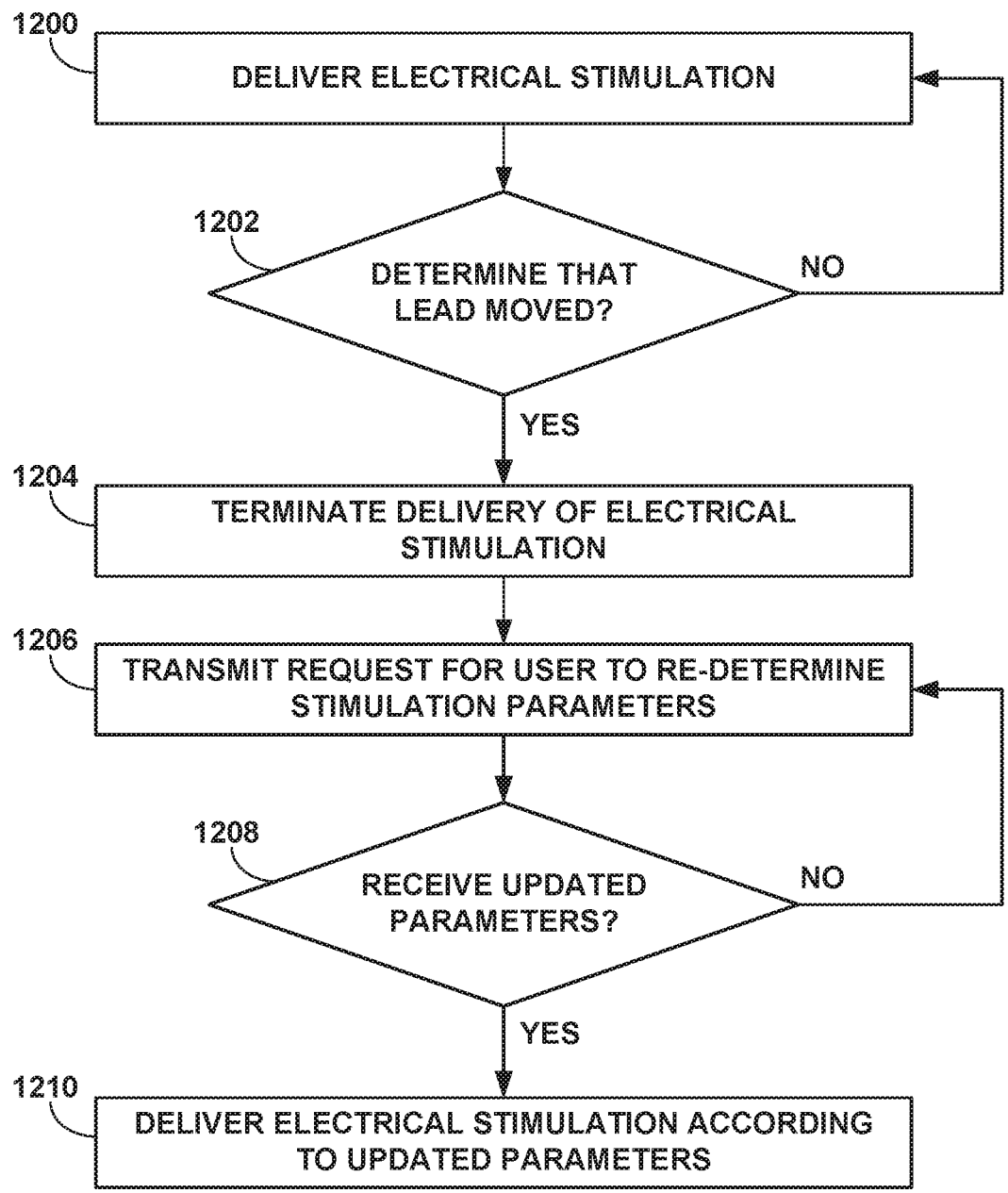
FIG. 12 is a flowchart illustrating an example technique for updating stimulation parameters in response to determining a lead has moved.

FIG. 12 is a flowchart illustrating an example technique for updating stimulation parameters in response to determining a lead has moved. FIG. 12 may be a technique for performing one or more actions as described in FIGS. 10 and 11. The technique of FIG. 11 will be described with respect to processor 210 of IMD 106 in FIG. 2. However, other processors, devices, or combinations thereof, may perform the techniques of FIG. 11 in other examples. As shown in FIG. 12, processor 210 controls IMD 106 to deliver electrical stimulation (1200). If processor 210 determines that a lead has not moved ("NO" branch of block 1202), processor 210 continues to deliver electrical stimulation according to one or more stored stimulation programs (1200).

If processor 210 determines that the lead has moved ("YES" branch of block 1202), processor 210 terminates delivery of electrical stimulation to the patient (1204). Processor 210 may terminate stimulation delivery because the stimulation may no longer be effective, or may even provide side effects to the patient. Alternatively, processor 210 may determine that lead moved, but that the moved lead, or the remaining parameters, are still within an acceptable operating range. In this manner, processor 210 may continue therapy and/or send a message to the clinician to re-evaluate stimulation parameters for therapy due to the movement. Processor 210 then transmits, to an external device such as programmer 104, a request for a user to re-determine stimulation parameters for the moved lead (1206). In some examples, this request may recommend one or more stimulation parameter values to accommodate how the lead has moved. If processor 210 does not receive updated stimulation parameters ("NO" branch of block 1208), processor 210 may retransmit the request for updated stimulation parameters (1206) or otherwise wait for updated stimulation parameters. Once processor 210 receives the updated stimulation parameters ("YES" branch of block 1208), processor 210 the controls IMD 106 to deliver electrical stimulation according to the stimulation parameter values received from the external device (1210).

One or more examples are described herein. Example 1: a method comprising: receiving, by processing circuitry, signal information indicative of first electrical signals sensed from a plurality of electrode combinations at a second time, each electrode combination comprising an electrode carried by a lead, wherein the lead defines a longitudinal axis and comprises a plurality of electrodes disposed at different positions around the longitudinal axis of the lead; determining, by the processing circuitry and based on the signal information and initial information indicative of second electrical signals sensed from the plurality of electrode combinations at a first time prior to the second time, that the lead has rotated with respect to tissue; and outputting, by the processing circuitry, an indication that the lead has rotated with respect to the tissue.

Example 2: the method of example 1, wherein determining that the lead has rotated comprises: comparing first amplitudes of the initial information for the plurality of electrode combinations to second amplitudes of the signal information for the plurality of electrode combinations; determining, based on the comparison, that the first amplitudes of the initial information do not match the second amplitudes of the signal information; and determining, based on determination that the first amplitudes do not match the second amplitudes, that the lead has rotated.

Example 3: the method of examples 1 or 2, wherein determining that the lead has rotated comprises: comparing first spectral power of the initial information for the plurality of electrode combinations to second spectral power of the signal information for the plurality of electrode combinations; determining, based on the comparison, that the first spectral power of the initial information do not match the second spectral power of the signal information; and determining, based on determination that the first spectral power do not match the second spectral power, that the lead has rotated.

Example 4: the method of any of examples 1 through 3, wherein the initial information comprises a first matrix representing signal amplitudes sensed by respective electrode combinations of the plurality of electrode combinations at the first time, and wherein the signal information comprises a second matrix representing signal amplitudes sensed by respective electrode combinations of the plurality of electrode combinations at the second time.

Example 5: the method of any of examples 1 through 4, wherein determining that the lead has rotated comprises determining that the signal information indicates that a first electrode combination of the plurality of electrode combinations sensed a second electrical signal at the second time having a second amplitude greater than a first amplitude of a first electrical signal sensed by the first electrode combination at the first time.

Example 6: the method of any of examples 1 through 5, wherein the first electrical signals and the second electrical signals comprise differential signals between respective electrode combinations of the plurality of electrode combinations.

Example 7: the method of any of examples 1 through 6, wherein the first electrical signals and the second electrical signals comprise monopolar signals between respective electrode combinations of the plurality of electrode combinations.

Example 8: the method of any of examples 1 through 7, further comprising: determining, based on the signal information and initial information indicative of second electrical signals sensed from the plurality of electrode combinations at a first time prior to the second time, that the lead has shifted longitudinally with respect to the tissue; and outputting an indication that the lead has shifted longitudinally with respect to the tissue.

Example 9: the method of any of examples 1 through 8, further comprising controlling a display to present the indication to a user that the lead has rotated with respect to the tissue.

Example 10: the method of any of examples 1 through 9, further comprising: transmitting a request to a user to update stimulation parameter values that define electrical stimulation; receiving updated stimulation parameters that define electrical stimulation; and controlling a medical device to deliver the electrical stimulation according to the updated stimulation parameters.

Example 11: the method of any of examples 1 through 10, wherein the plurality of electrodes comprises: a first set of three electrodes disposed at different respective positions around the longitudinal axis of the lead and at a first longitudinal position along the lead; a second set of three electrodes disposed at a second longitudinal position along the lead different than the first longitudinal position; and at least one ring electrode disposed at a third longitudinal position along the lead different than the first longitudinal position and the second longitudinal position.

Example 12: a system comprising: a memory configured to store initial information indicative of first electrical signals sensed from a plurality of electrode combinations at a first time, each electrode combination comprising an electrode carried by a lead, wherein the lead defines a longitudinal axis and comprises a plurality of electrodes disposed at different positions around the longitudinal axis of the lead; and processing circuitry configured to: receive signal information indicative of second electrical signals sensed from the plurality of electrode combinations at a second time after the first time; determine, based on the signal information, that the lead has rotated with respect to tissue; and output, an indication that the lead has rotated with respect to the tissue.

Example 13: the system of example 12, wherein the processing circuitry is configured to determine that the lead has rotated by: comparing first amplitudes of the initial information for the plurality of electrode combinations to second amplitudes of the signal information for the plurality of electrode combinations; determining, based on the comparison, that the first amplitudes of the initial information do not match the second amplitudes of the signal information; and determining, based on determination that the first amplitudes do not match the second amplitudes, that the lead has rotated.

Example 14: the system of examples 12 or 13, wherein the processing circuitry is configured to determine that the lead has rotated by: comparing first spectral power of the initial information for the plurality of electrode combinations to second spectral power of the signal information for the plurality of electrode combinations; determining, based on the comparison, that the first spectral power of the initial information do not match the second spectral power of the signal information; and determining, based on determination that the first spectral power do not match the second spectral power, that the lead has rotated.

Example 15: the system of any of examples 12 through 14, wherein the initial information comprises a first matrix representing signal amplitudes sensed by respective electrode combinations of the plurality of electrode combinations at the first time, and wherein the signal information comprises a second matrix representing signal amplitudes sensed by respective electrode combinations of the plurality of electrode combinations at the second time.

Example 16: the system of any of examples 12 through 15, wherein the processing circuitry is configured to determine that the lead has rotated by determining that the signal information indicates that a first electrode combination of the plurality of electrode combinations sensed a second electrical signal at the second time having a second amplitude greater than a first amplitude of a first electrical signal sensed by the first electrode combination at the first time.

Example 17: the system of any of examples 12 through 16, wherein the first electrical signals and the second electrical signals comprise differential signals between respective electrode combinations of the plurality of electrode combinations.

Example 18: the system of any of examples 12 through 17, wherein the first electrical signals and the second electrical signals comprise monopolar signals between respective electrode combinations of the plurality of electrode combinations.

Example 19: the system of any of examples 12 through 18, wherein the processing circuitry is configured to: determine, based on the signal information and initial information indicative of second electrical signals sensed from the plurality of electrode combinations at a first time prior to the second time, that the lead has shifted longitudinally with respect to the tissue; and output an indication that the lead has shifted longitudinally with respect to the tissue.

Example 20: the system of any of examples 12 through 19, wherein the processing circuitry is configured to control a display to present the indication to a user that the lead has rotated with respect to the tissue.

Example 21: the system of any of examples 12 through 20, wherein the processing circuitry is configured to: transmit a request to a user to update stimulation parameter values that define electrical stimulation; receive updated stimulation parameters that define electrical stimulation; and control a medical device to deliver the electrical stimulation according to the updated stimulation parameters.

Example 22: the system of any of examples 12 through 21, wherein the plurality of electrodes comprises: a first set of three electrodes disposed at different respective positions around the longitudinal axis of the lead and at a first longitudinal position along the lead; a second set of three electrodes disposed at a second longitudinal position along the lead different than the first longitudinal position; and at least one ring electrode disposed at a third longitudinal position along the lead different than the first longitudinal position and the second longitudinal position.

Example 23: the system of any of examples 12 through 22, wherein an implantable medical device comprises the memory and the processing circuitry, and wherein the implantable medical device is configured to couple with the plurality of electrodes.

Example 24: a computer-readable storage medium comprising instructions that, when executed, cause processing circuitry to: receive signal information indicative of first electrical signals sensed from a plurality of electrode combinations at a second time, each electrode combination comprising an electrode carried by a lead, wherein the lead defines a longitudinal axis and comprises a plurality of electrodes disposed at different positions around the longitudinal axis of the lead; determine, based on the signal information and initial information indicative of second electrical signals sensed from the plurality of electrode combinations at a first time prior to the second time, that the lead has rotated with respect to tissue; and output an indication that the lead has rotated with respect to the tissue.

The techniques described in this disclosure may be implemented, at least in part, in hardware, software, firmware or any combination thereof. For example, various aspects of the described techniques may be implemented within one or more processors, such as fixed function processing circuitry and/or programmable processing circuitry, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit comprising hardware may also perform one or more of the techniques of this disclosure.

Such hardware, software, and firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in a computer-readable medium, such as a computer-readable storage medium, containing instructions. Instructions embedded or encoded in a computer-readable storage medium may cause a programmable processor, or other processor, to perform the method, e.g., when the instructions are executed. Computer readable storage media may include random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

Various examples have been described. These and other examples are within the scope of the following claims.

What is claimed is:

1. A method comprising:
receiving, by processing circuitry, signal information indicative of first electrical signals sensed from a brain tissue and by a plurality of electrode combinations at a second time, each electrode combination comprising an electrode carried by a lead, wherein the lead defines a longitudinal axis and comprises a plurality of electrodes disposed at different circumferential positions around the longitudinal axis of the lead;
determining, by the processing circuitry and based on the signal information and initial information indicative of second electrical signals sensed from the plurality of electrode combinations at a first time prior to the second time, that the lead has rotated with respect to the brain tissue; and
outputting, by the processing circuitry, an indication that the lead has rotated with respect to the brain tissue.

2. The method of claim 1, wherein determining that the lead has rotated comprises:
comparing first amplitudes of the initial information for the plurality of electrode combinations to second amplitudes of the signal information for the plurality of electrode combinations;
determining, based on the comparison, that the first amplitudes of the initial information do not match the second amplitudes of the signal information; and
determining, based on determination that the first amplitudes do not match the second amplitudes, that the lead has rotated.

3. The method of claim 1, wherein determining that the lead has rotated comprises:
comparing first spectral power of the initial information for the plurality of electrode combinations to second spectral power of the signal information for the plurality of electrode combinations;
determining, based on the comparison, that the first spectral power of the initial information do not match the second spectral power of the signal information; and
determining, based on determination that the first spectral power do not match the second spectral power, that the lead has rotated.

4. The method of claim 1, wherein the initial information comprises a first matrix representing signal amplitudes sensed by respective electrode combinations of the plurality of electrode combinations at the first time, and wherein the signal information comprises a second matrix representing signal amplitudes sensed by respective electrode combinations of the plurality of electrode combinations at the second time.

5. The method of claim 1, wherein determining that the lead has rotated comprises determining that the signal information indicates that a first electrode combination of the plurality of electrode combinations sensed a second electrical signal at the second time having a second amplitude greater than a first amplitude of a first electrical signal sensed by the first electrode combination at the first time.

6. The method of claim 1, wherein the first electrical signals and the second electrical signals comprise differential signals between respective electrode combinations of the plurality of electrode combinations.

7. The method of claim 1, wherein the first electrical signals and the second electrical signals comprise monopolar signals between respective electrode combinations of the plurality of electrode combinations.

8. The method of claim 1, further comprising:
determining, based on the signal information and initial information indicative of second electrical signals sensed from the plurality of electrode combinations at a first time prior to the second time, that the lead has shifted longitudinally with respect to the brain tissue; and
outputting an indication that the lead has shifted longitudinally with respect to the brain tissue.

9. The method of claim 1, further comprising controlling a display to present the indication to a user that the lead has rotated with respect to the brain tissue.

10. The method of claim 1, further comprising:
transmitting a request to a user to update stimulation parameter values that define electrical stimulation;
receiving updated stimulation parameters that define electrical stimulation; and
controlling a medical device to deliver the electrical stimulation according to the updated stimulation parameters.

11. The method of claim 1, wherein the plurality of electrodes comprises:
a first set of three electrodes disposed at different respective positions around the longitudinal axis of the lead and at a first longitudinal position along the lead;
a second set of three electrodes disposed at a second longitudinal position along the lead different than the first longitudinal position; and
at least one ring electrode disposed at a third longitudinal position along the lead different than the first longitudinal position and the second longitudinal position.

12. A system comprising:
a memory configured to store initial information indicative of first electrical signals sensed from a brain tissue and by a plurality of electrode combinations at a first time, each electrode combination comprising an electrode carried by a lead, wherein the lead defines a longitudinal axis and comprises a plurality of electrodes disposed at different circumferential positions around the longitudinal axis of the lead; and processing circuitry configured to:
- receive signal information indicative of second electrical signals sensed from the plurality of electrode combinations at a second time after the first time;
- determine, based on the signal information, that the lead has rotated with respect to brain tissue; and
- output an indication that the lead has rotated with respect to the brain tissue.

13. The system of claim 12, wherein the processing circuitry is configured to determine that the lead has rotated by:
- comparing first amplitudes of the initial information for the plurality of electrode combinations to second amplitudes of the signal information for the plurality of electrode combinations;
- determining, based on the comparison, that the first amplitudes of the initial information do not match the second amplitudes of the signal information; and
- determining, based on determination that the first amplitudes do not match the second amplitudes, that the lead has rotated.

14. The system of claim 12, wherein the processing circuitry is configured to determine that the lead has rotated by:
- comparing first spectral power of the initial information for the plurality of electrode combinations to second spectral power of the signal information for the plurality of electrode combinations;
- determining, based on the comparison, that the first spectral power of the initial information do not match the second spectral power of the signal information; and
- determining, based on determination that the first spectral power do not match the second spectral power, that the lead has rotated.

15. The system of claim 12, wherein the initial information comprises a first matrix representing signal amplitudes sensed by respective electrode combinations of the plurality of electrode combinations at the first time, and wherein the signal information comprises a second matrix representing signal amplitudes sensed by respective electrode combinations of the plurality of electrode combinations at the second time.

16. The system of claim 12, wherein the processing circuitry is configured to determine that the lead has rotated by determining that the signal information indicates that a first electrode combination of the plurality of electrode combinations sensed a second electrical signal at the second time having a second amplitude greater than a first amplitude of a first electrical signal sensed by the first electrode combination at the first time.

17. The system of claim 12, wherein the first electrical signals and the second electrical signals comprise differential signals between respective electrode combinations of the plurality of electrode combinations.

18. The system of claim 12, wherein the first electrical signals and the second electrical signals comprise monopolar signals between respective electrode combinations of the plurality of electrode combinations.

19. The system of claim 12, wherein the processing circuitry is configured to:
- determine, based on the signal information and initial information indicative of second electrical signals sensed from the plurality of electrode combinations at a first time prior to the second time, that the lead has shifted longitudinally with respect to the brain tissue; and
- output an indication that the lead has shifted longitudinally with respect to the brain tissue.

20. The system of claim 12, wherein the processing circuitry is configured to control a display to present the indication to a user that the lead has rotated with respect to the brain tissue.

21. The system of claim 12, wherein the processing circuitry is configured to:
- transmit a request to a user to update stimulation parameter values that define electrical stimulation;
- receive updated stimulation parameters that define electrical stimulation; and
- control a medical device to deliver the electrical stimulation according to the updated stimulation parameters.

22. The system of claim 12, wherein the plurality of electrodes comprises:
- a first set of three electrodes disposed at different respective positions around the longitudinal axis of the lead and at a first longitudinal position along the lead;
- a second set of three electrodes disposed at a second longitudinal position along the lead different than the first longitudinal position; and
- at least one ring electrode disposed at a third longitudinal position along the lead different than the first longitudinal position and the second longitudinal position.

23. The system of claim 12, wherein an implantable medical device comprises the memory and the processing circuitry, and wherein the implantable medical device is configured to couple with the plurality of electrodes.

24. A computer-readable storage medium comprising instructions that, when executed, cause processing circuitry to:
- receive signal information indicative of first electrical signals sensed from a brain tissue and by a plurality of electrode combinations at a second time, each electrode combination comprising an electrode carried by a lead, wherein the lead defines a longitudinal axis and comprises a plurality of electrodes disposed at different circumferential positions around the longitudinal axis of the lead;
- determine, based on the signal information and initial information indicative of second electrical signals sensed from the plurality of electrode combinations at a first time prior to the second time, that the lead has rotated with respect to brain tissue; and
- output an indication that the lead has rotated with respect to the brain tissue.

* * * * *